(12) United States Patent
Noguchi et al.

(10) Patent No.: US 7,582,056 B2
(45) Date of Patent: Sep. 1, 2009

(54) ENDOSCOPE SYSTEM

(75) Inventors: Toshiaki Noguchi, Tachikawa (JP); Hitoshi Hasegawa, Yokohama (JP); Masanori Gocho, Hachioji (JP); Eiri Suzuki, Sagamihara (JP); Hisashi Kuroshima, Hachioji (JP)

(73) Assignee: Olympus Corporation, Tokyo (JP)

( * ) Notice: Subject to any disclaimer, the term of this patent is extended or adjusted under 35 U.S.C. 154(b) by 554 days.

(21) Appl. No.: 11/327,706

(22) Filed: Jan. 6, 2006

(65) Prior Publication Data
US 2006/0116550 A1 Jun. 1, 2006

Related U.S. Application Data

(63) Continuation of application No. PCT/JP2004/001635, filed on Feb. 16, 2004.

(51) Int. Cl.
*A61B 1/04* (2006.01)
(52) U.S. Cl. .................. 600/132; 600/110; 600/109
(58) Field of Classification Search .................. 600/132, 600/178, 109, 110
See application file for complete search history.

(56) References Cited

U.S. PATENT DOCUMENTS

| 4,416,268 | A | | 11/1983 | Hagino | |
|---|---|---|---|---|---|
| 5,335,662 | A | * | 8/1994 | Kimura et al. | 600/459 |
| 5,716,323 | A | * | 2/1998 | Lee | 600/134 |
| 6,099,465 | A | * | 8/2000 | Inoue | 600/134 |
| 6,319,197 | B1 | * | 11/2001 | Tsuji et al. | 600/132 |
| 7,018,331 | B2 | * | 3/2006 | Chang et al. | 600/182 |
| 2003/0018238 | A1 | | 1/2003 | Obata et al. | |
| 2004/0104999 | A1 | * | 6/2004 | Okada | 348/65 |
| 2004/0171913 | A1 | * | 9/2004 | Saruya | 600/132 |
| 2005/0033116 | A1 | * | 2/2005 | Miyake et al. | 600/109 |
| 2005/0070761 | A1 | * | 3/2005 | Higuchi | 600/109 |
| 2005/0222499 | A1 | * | 10/2005 | Banik et al. | 600/132 |

(Continued)

FOREIGN PATENT DOCUMENTS

JP 06-121767 5/1994

(Continued)

OTHER PUBLICATIONS

Patent Abstracts of Japan, Japanese Publication No. 2003-127085, dated May 8, 2003.

*Primary Examiner*—John P Leubecker
(74) *Attorney, Agent, or Firm*—Scully, Scott, Murphy & Presser, P.C.

(57) ABSTRACT

An endoscope system includes an endoscope having an image pickup device, a control unit, signal lines, a first earth electric wire, a light guide and a scope connector. The scope connector is formed by collecting a first electric contact, a first non-contact power transmitting portion serving as a non-contact electromagnetic induction and coupling device, a first non-contact signal transmitting portion, and a first illumination light transmitting portion. The system further includes an endoscope control device having a multi-connector portion to which the scope connector is detachably connected, a second electrical contact, which is provided in the multi-connector portion and connectable to the first electric contact, a second non-contact power transmitting portion and a second non-contact signal transmitting portion which are provided in the multi-connector portion and connectable to the first non-contact power transmitting portion and the first non-contact signal transmitting portion respectively, and a video signal processing unit for controlling the control unit of the endoscope.

8 Claims, 19 Drawing Sheets

U.S. PATENT DOCUMENTS

2007/0185385 A1* 8/2007 Noguchi et al. .............. 600/132
2008/0058598 A1* 3/2008 Ries et al. .................... 600/132

FOREIGN PATENT DOCUMENTS

| JP | 10-295635 | 11/1998 |
| JP | 11-216115 | 8/1999 |
| JP | 2000-225093 | 8/2000 |
| JP | 2002-125926 | 5/2002 |
| JP | 2002-219102 | 8/2002 |
| JP | 2003-135366 | 5/2003 |
| JP | 2003-325443 | 11/2003 |
| WO | WO 98/52350 | 11/1998 |
| WO | WO 02/09577 A2 | 2/2002 |

* cited by examiner

ENDOSCOPE SYSTEM

CROSS REFERENCE TO RELATED APPLICATION

This application is a continuation application of PCT/JP2004/001635 filed on Feb. 16, 2004 the disclosure of which is incorporated herein by its reference.

BACKGROUND OF THE INVENTION

1. Field of the Invention

The present invention relates to an endoscope system comprising an endoscope having an inserting portion inserted in the body cavity, which is re-used by cleaning and sterilizing the inserting portion after ending the examination and treatment.

2. Description of the Related Art

Referring to FIG. 1, a conventional endoscope 1 mainly comprises: an operating portion 2; an inserting portion 3; and a universal cord 4. The endoscope 1 includes various inserting channels shown in FIG. 2, such as an air/water feed channel 1a, a treatment tool channel 1c which is also used for a suction channel 1b, an air feed channel 1d, and water feed channel 1e, and various signal lines, an electric wire, and a light guide fiber (not shown).

The universal cord 4 comprises a scope connector 5 at the proximal end portion. The scope connector 5 comprises: an electric connector 5a; a light guide connector 5b; and an air feed cap 5c or a suction cap 5d. An endoscope control device (not shown) as an external device of the endoscope 1 is electrically connected to the electric connector 5a. A light source device for endoscope as an external device is connected to the light guide connector 5b.

Referring to FIGS. 1 and 2, the electric connector 5a has the structure for attaching a waterproof cap 6. That is, upon cleaning and sterilization of the endoscope 1, the waterproof cap 6 is attached to the electric connector 5a. Thus, the waterproof property of the electric connector 5a is ensured.

The operating portion 2 comprises: an air/water feed button 7 for controlling the air/water feed operation by the hand of an operator; and a suction button 8 for controlling the suction. The air/water feed button 7 is attached to an air/water feed cylinder 9a, and the suction button 8 is attached to a suction cylinder 9b.

Further, the operating portion 2 comprises a branched portion 10 which is formed by branching a part of the suction channel 1b on the inserting portion 3 side. The branched portion 10 comprises a clamp port 11 for inserting and pulling out a treatment tool for treatment during the operation. The clamp port 11 is closed by a clamp stopper 12 having a slit 12a into which the treatment tool can be inserted. On the distal-end portion, that is, on the distal-end surface shown in FIG. 2, the inserting portion 3 comprises an air/water feed opening 3a for feeding air/water and a treatment tool opening 3b which functions as a suction opening and a portion for introducing the treatment tool. The end portion of an air/water feed channel 1a is communicated with the air/water feed opening 3a, and the end portion of the treatment tool channel 1c is communicated with the treatment tool opening 3b.

Upon cleaning and sterilizing the endoscope 1 with the above-mentioned structure after finishing the examination or the like, the endoscope 1 is cleaned and sterilized in accordance with the structure of the endoscope 1 as follows. That is, in order to clean and sterilize the air/water feed channel 1a, suction channel 1b, treatment tool channel 1c, air feed channel 1d, and water feed channel 1e of the endoscope 1, a cleaning brush 13 is inserted from cylinders 9a and 9b as one opening thereof or the clamp port 11, and is further projected from the air/water feed opening 3a, treatment tool opening 3b, and/or suction cap 5d as another opening thereof, thereby cleaning the channels.

Japanese Unexamined Patent Application Publication No. 2000-225093 discloses an endoscope system having a channel, in which an air feed channel and a water feed channel are easily cleaned and a channel is connected to an electromagnetic valve unit without using an externally-exposed flexible tube.

In the endoscope system disclosed in Japanese Unexamined Patent Application Publication No. 2000-225093, a connecting end of a light guide, a connecting port of the air feed channel, and a connecting port of the water feed channel are arranged in a lump in a connector portion (corresponding to the scope connector 5 shown in FIG. 1) of a cable (corresponding to the universal cord 4 shown in FIG. 1). Further, the air feed channel and the water feed channel in the connector portion are straightly formed and arranged to the cable. The connector portion is connected to a light source/electromagnetic valve device (corresponding to the endoscope control device). Further, the air feed channel and the water feed channel in the endoscope are formed as independent channels from the distal-end portion to the connector.

SUMMARY OF THE INVENTION

According to the present invention, an endoscope system comprises: an endoscope comprising at least a main body unit formed by collecting an electric function portion, an optical function portion, and channels to a part of the main body unit, a signal line which is detachable to the main body unit and which is extended from the electric function portion of the main body unit, and a universal cord unit comprising a scope connector at an end portion of the universal cord unit in which a light guide extended from the optical function portion is inserted; and an endoscope control device comprising at least a multi-connector portion to which the scope connector of the universal cord unit is detachably arranged, a signal processing unit which controls the electric function portion of the endoscope, a light source device which controls the optical function portion of the endoscope, a light source control unit, and a power supply unit for lighting-on a lamp. Thus, when the universal cord unit is attached to the main body unit, illuminating light is irradiated to the target portion, thereby performing the normal observation. For example, after using the endoscope, the universal cord unit is detached from the main body unit and, consequently, channels in the universal cord unit do not need to be cleaned.

Other features and advantages of the invention will become more clearly understood from the following description referring to the accompanying drawings.

DETAILED DESCRIPTION OF THE PREFERRED EMBODIMENT(S)

The present invention will be described in detail with reference to the attached drawings.

The first embodiment of the present invention will be described with reference to FIGS. 3 to 8.

Figure 1:
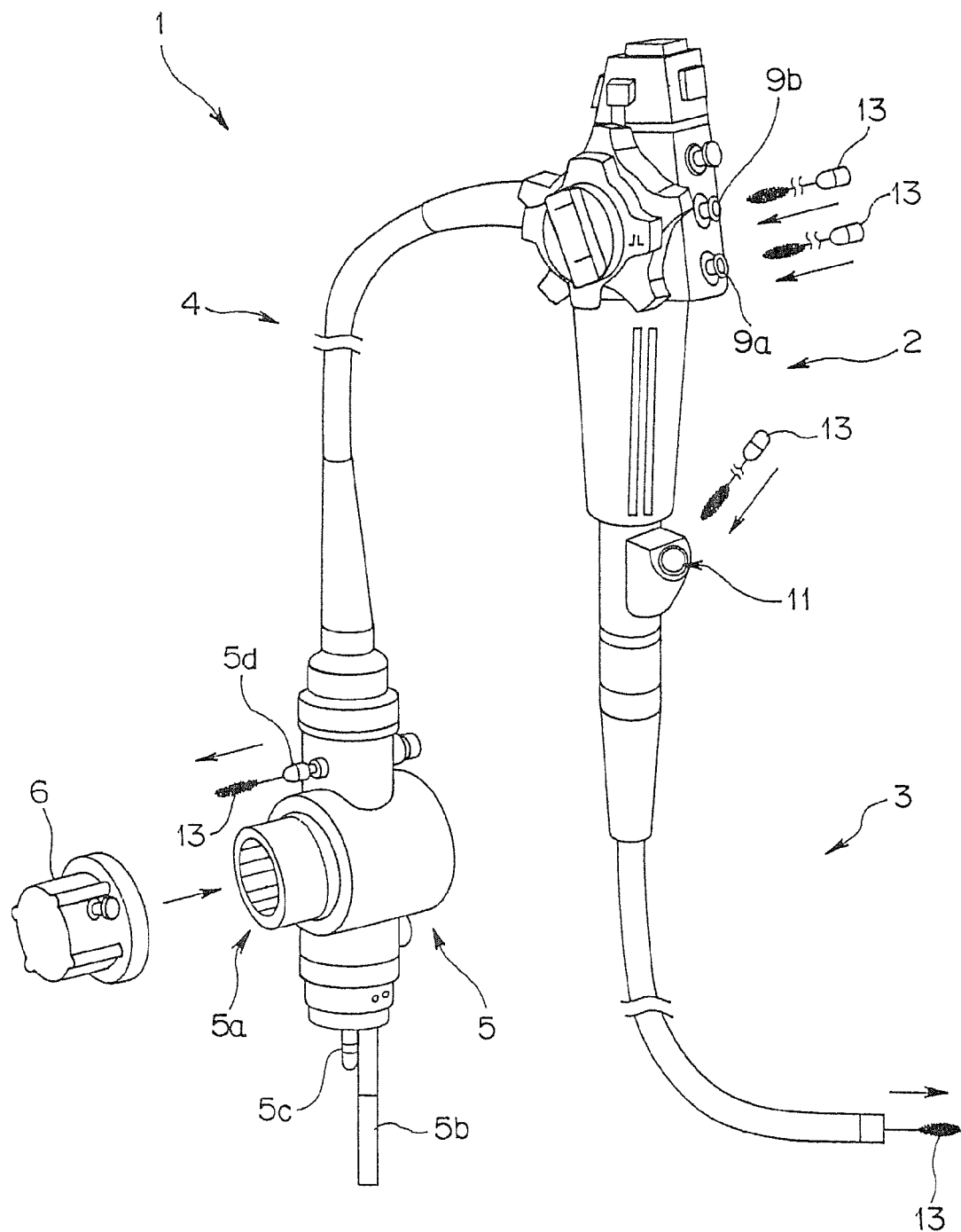
FIG. 1 is a diagram showing a conventional endoscope.
Figure 2:
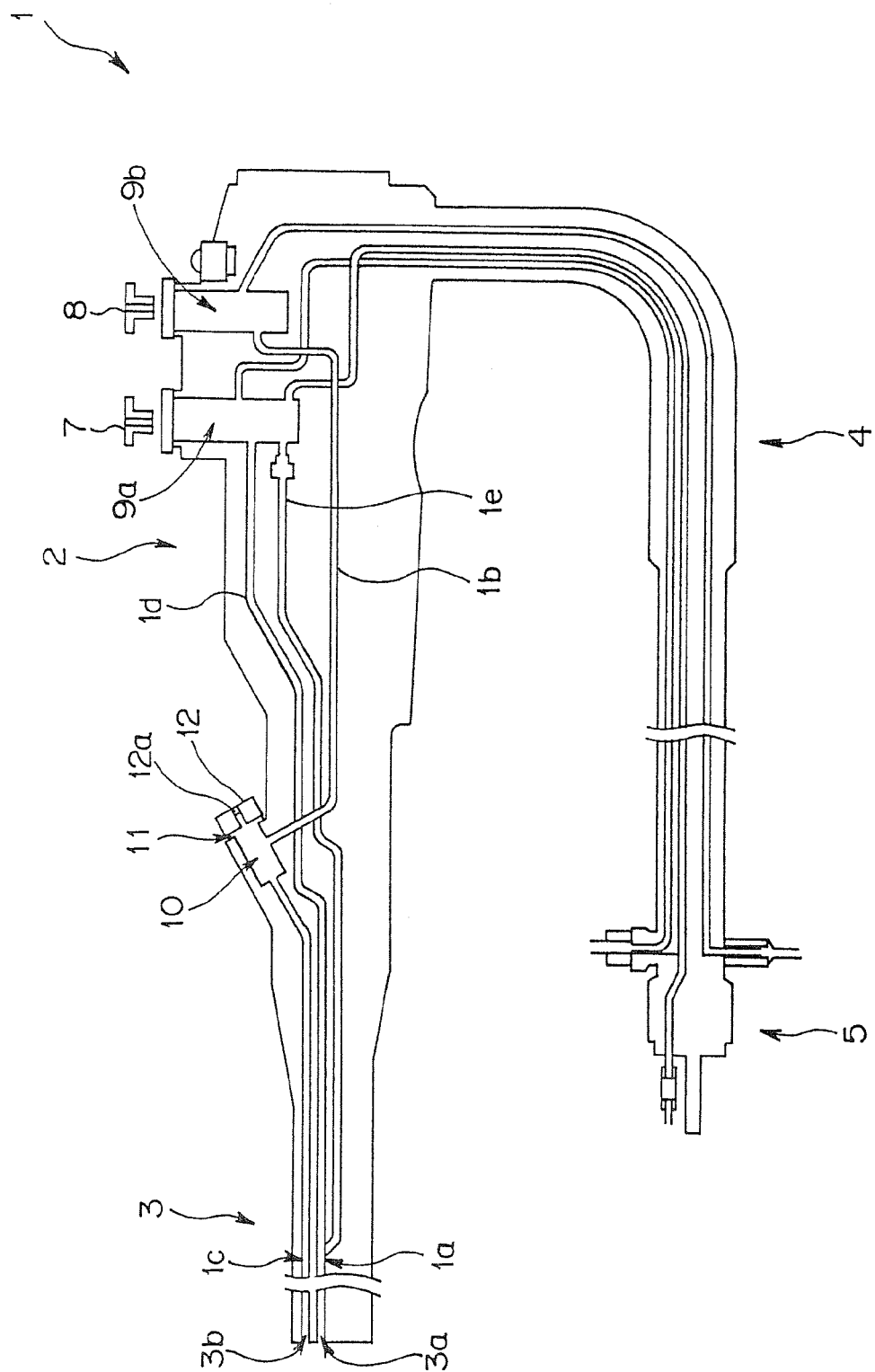
FIG. 2 is a diagram for explaining channels arranged in the conventional endoscope.
Figure 3:
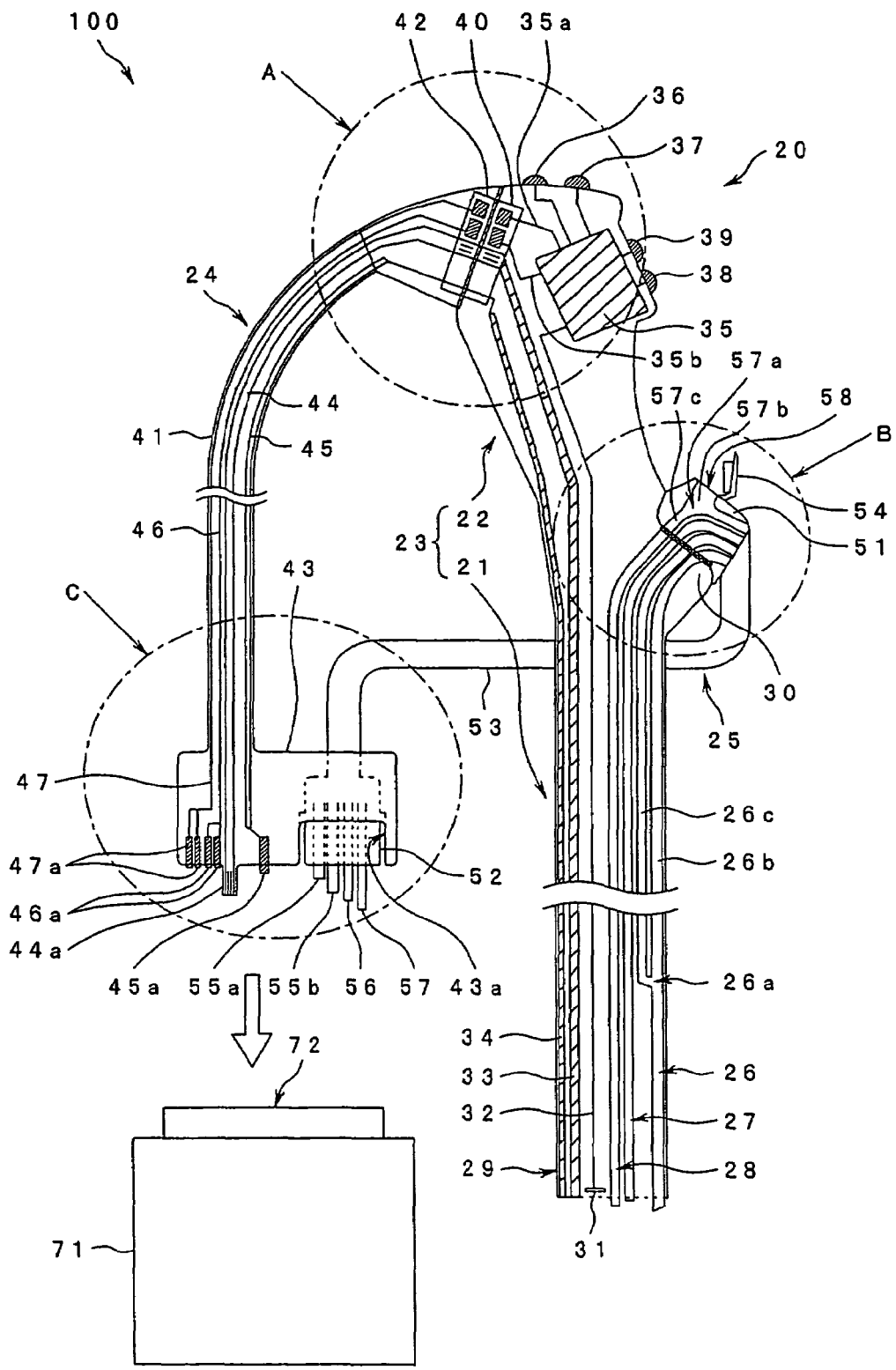
FIG. 3 is a diagram for explaining the structure of an endoscope system according to the first embodiment of the present invention.

Referring to FIG. 3, an endoscope system 100 according to the first embodiment mainly comprises: an endoscope 20; and an endoscope control device 71. A multi-connector 72 is arranged to the endoscope control device 71, as will be described later.

The endoscope 20 comprises: a main-body-portion unit 23 comprising a slender and flexible endoscope inserting portion (hereinafter, abbreviated to an inserting portion) 21 and an endoscope operating portion (hereinafter, abbreviated to an operating portion) 22; a universal cord unit (hereinafter, abbreviated to a cord unit) 24; and a channel unit 25.

The main-body-portion unit 23 is detachably connected to the cord unit 24 by a connecting portion A shown in FIG. 3. Further, the main-body-portion unit 23 is detachably connected to the channel unit 25 by a connecting portion B shown in FIG. 3. Furthermore, the cord unit 24 is detachably connected to the channel unit 25 by a connecting portion C shown in FIG. 3.

Accordingly, upon using endoscope 20, all of the main-body-portion unit 23, the cord unit 24, and the channel unit 25 are connected as shown in FIG. 3. On the other hand, upon cleaning and sterilization after ending the endoscope examination, the main-body-portion unit 23, the cord unit 24, and the channel unit 25 are detached, respectively, as will be described later with reference to FIG. 5. The detached channel unit 25 is disposed, and the main-body-portion unit 23 and the cord unit 24 are cleaned and sterilized. That is, the channel unit 25 is disposable.

A description is given of the structures of the main-body-portion unit 23, the cord unit 24, and the channel unit 25.

First, the structure of the main-body-portion unit 23 will be described.

The inserting portion 21 of the main-body-portion unit 23 comprises as channels: an air/water feed channel 26; a front water feed sub-channel 27; and a suction channel 28. The air/water feed channel 26 feeds the air in the body cavity upon endoscope examination, feeds water for cleaning an optical lens cover (not shown) arranged to the endoscope distal-end portion. The air/water feed channel 26 includes a branched portion 26a in the halfway, and are branched into two channels 26b and 26c. The front water feed sub-channel 27 preferably assures an observing field-of-view by feeding the water to an observed portion in the body cavity. The suction channel 28 is a channel for inserting a treatment tool which sucks waste in the body cavity during the examination, or which collects the organ in the affected part in the body cavity (also referred to biopsy). One end of each of the air/water feed channel 26, front water feed sub-channel 27, and suction channel 28 is arranged at a distal-end portion 29 of the inserting portion 21. While, the other end of each of the channels 26b, 26c, front water feed sub-channel 27, and suction channel 28 is collected to a channel unit connecting portion 30 which is formed to the side surface of the proximal end portion of the inserting portion near the boundary portion with the operating portion 22. The air/water feed channel 26, front water feed sub-channel 27, and suction channel 28 reaching the channel unit connecting portion 30 from the distal-end portion 29 are straightly inserted in the inserting portion 21.

The distal-end portion 29 of the inserting portion 21 includes a charge-coupled device (hereinafter, abbreviated to a CCD) 31 for picking-up an endoscope image. A CCD signal line 32 for transmitting a driving signal and an electric signal photoelectrically-converted is extended from the CCD 31. At the distal-end portion 29, the distal portion of a light guide 33 for supplying illuminating light faces an illuminating optical system (not shown). Further, an earth electric wire 34 which functions as an earth for ensuring the electric safety upon using the electric knife for electric treatment is arranged at the distal-end portion 29.

The CCD signal line 32 is electrically connected to a control unit 35 shown by hatched lines in FIG. 3, arranged in the operating portion 22, via the inserting portion 21 and the operating portion 22. The control unit 35 includes a power supply circuit, a control circuit for controlling the angle of a bending portion, and peripheral circuits such as a driving processing circuit for driving/processing various sensor signals, in addition to a signal processing circuit for processing an electric signal for the CCD. A zoom switch 36, a freeze switch 37, an air/water feed switch 38, and a suction switch 39 are arranged to the operating portion 22, and are electrically connected to the control unit 35.

The zoom switch 36 instructs the enlargement of the observed image which is displayed on the screen of a display device (not shown) upon the endoscope examination. The freeze switch 37 instructs the freezing operation of the observed image. The air/water feed switch 38 controls the air/water feed operation. The suction switch 39 controls the suction operation. Connecting means between the main-body-portion unit 23 and the cord unit 24 has a magnet structure or mechanical connector structure.

Signal lines 35a and 35b are extended from the control unit 35. The signal lines 35a and 35b, the proximal end portion of the earth electric wire 34, and the proximal end portion of the light guide 33 are collected to a cord unit connecting portion (hereinafter, abbreviated to a cord connecting portion) 40 which is formed to the side surface of the proximal end portion of the operating portion 22.

Although an illustration and a description are not shown in FIG. 3, angle operating means is arranged to the main-body-portion unit 23. The angle operating means operates the distal-end portion 29 of the inserting portion 21 in the up/down direction or left/right direction, and includes a bending portion formed by connecting a plurality of bending pieces in contact therewith, an angle wire, an angle lever, and an angle lock lever. The structure and the operation of the angle operation means have the same structures as those of the conventional endoscope.

Next, the structure of the cord unit 24 will be described.

The cord unit 24 comprises: a cord portion 41 which is slender and flexible; a main-body-portion unit connecting portion (hereinafter, abbreviated to a main body unit connecting portion) 42; and a scope connector 43. The scope connector 43 has a connector arranging portion 43a. A second channel-connector portion 52 of the channel unit 25, which will be described later, is detachably arranged to the connector arranging portion 43a. A light guide 44, an earth electric wire 45 for electric knife, a signal line 46, and a power supply line 47 are inserted into the cord unit 24.

The main body unit connecting portion 42 is detachably connected to the cord connecting portion 40 arranged to the main-body-portion unit 23. The scope connector 43 is detachably connected to a multi-connector 72. A power supply terminal 47a, a signal transfer terminal 46a, an earth terminal (hereinafter, abbreviated to an E terminal) 45a, and a light guide connector 44a are arranged to the scope connector 43.

Next, the structure of the channel unit 25 will be described.

The channel unit 25 is disposable. The channel unit 25 mainly comprises: a first channel-connector portion 51; a second channel-connector portion 52; and a channel main body 53 with flexibility. A clamp stop 54 is arranged to the first channel-connector portion 51. The channel unit 25 comprises: a first channel 55a and a second channel 55b which are communicated with the branched portions 26a and 26b forming the proximal-end portion side of the air/water feed channel 26; a third channel 56 which is communicated with the front water feed sub-channel 27; and a fourth channel 57 which is communicated with the suction channel 28.

The first channel-connector portion 51 is detachable to the channel unit connecting portion 30 formed to the main-body-portion unit 23. The first channel-connector portion 51 comprises a detaching portion which is driven by elastic force of an elastic member such as rubber or silicone, or by magnetic force of magnet, and which comprises a mechanical connecting portion containing a resin member or metallic member. Therefore, the channel unit connecting portion 30 is detached from the first channel-connector portion 51 by one touch.

By connecting the first channel-connector portion 51 to the channel unit connecting portion 30, the first channel 55a, the second channel 55b, the third channel 56, and the fourth channel 57 are communicated with the branched portion 26a, the channel 26b, the front water feed sub-channel 27, and the suction channel 28, respectively.

The treatment tool is inserted/pulled-out to/from an opening portion 58. The opening portion 58 is arranged to the first channel-connector portion 51. A branched portion 57a is formed to the fourth channel 57 at the first channel-connector portion 51. Therefore, the fourth channel 57 is branched into a first hole 57b communicated with the opening portion 58 at the branched portion 57a and a second hole 57c communicated with the suction channel 28.

The clamp stop 54 is arranged to the first channel-connector portion 51 so as to cover the opening portion 58. The clamp stop 54 closes the opening portion 58 upon endoscope observation. Upon using the treatment tool during endoscope observation, the treatment tool is inserted from a slit (not shown) arranged to the clamp stop 54.

End portions of the first channel 55a, second channel 55b, third channel 56, and fourth channel 57 are projected from the end surfaces of the second channel-connector portion 52. The second channel-connector portion 52 is detachably arranged to the connector arranging portion 43a formed to the scope connector 43.

The structure of the connecting portion will be described with reference to FIGS. 3 to 7.

Figure 4:
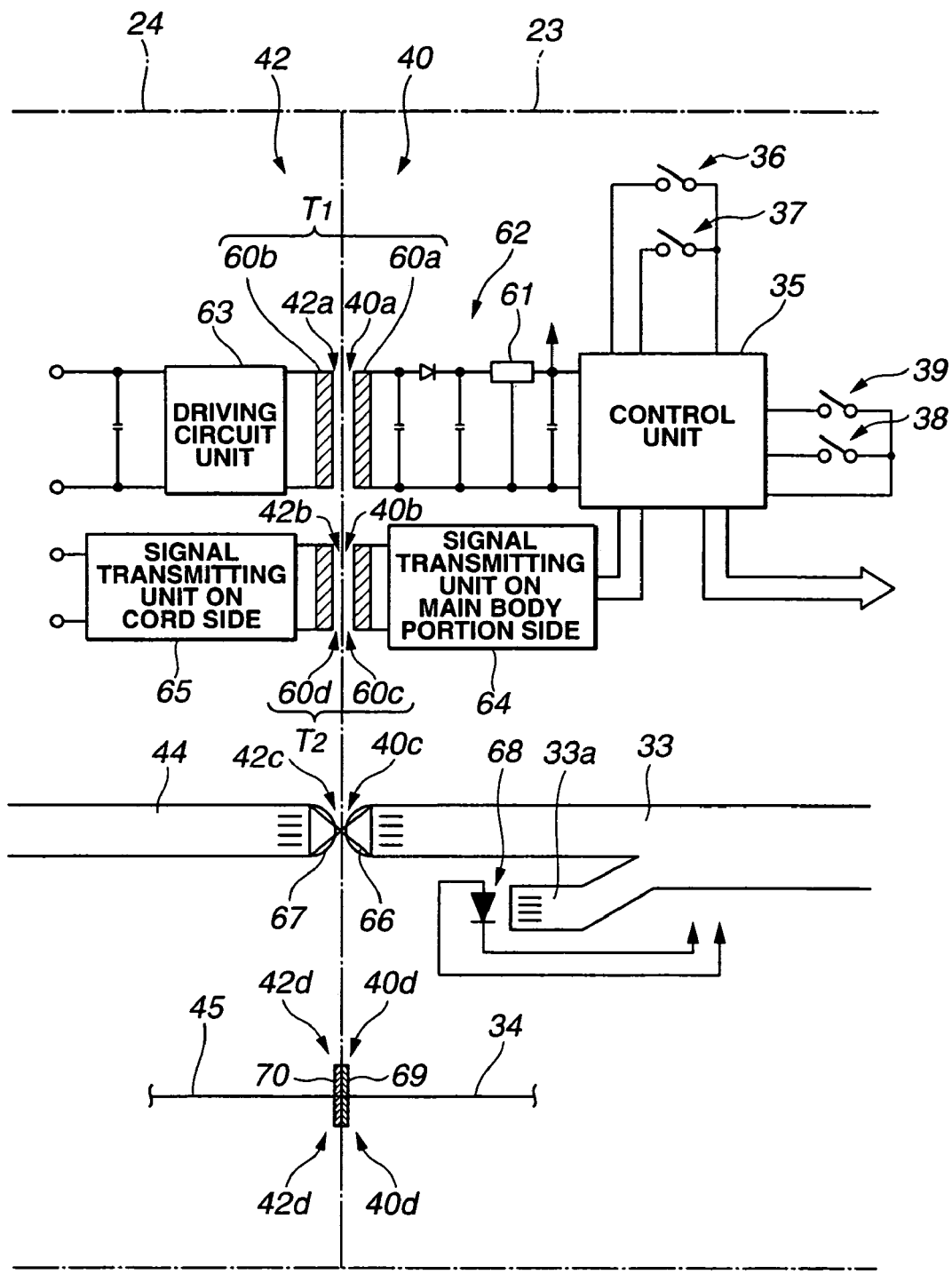
FIG. 4 is a block diagram for explaining the structure of a connecting portion between a main-body-portion unit and a universal cord unit.
Figure 5:
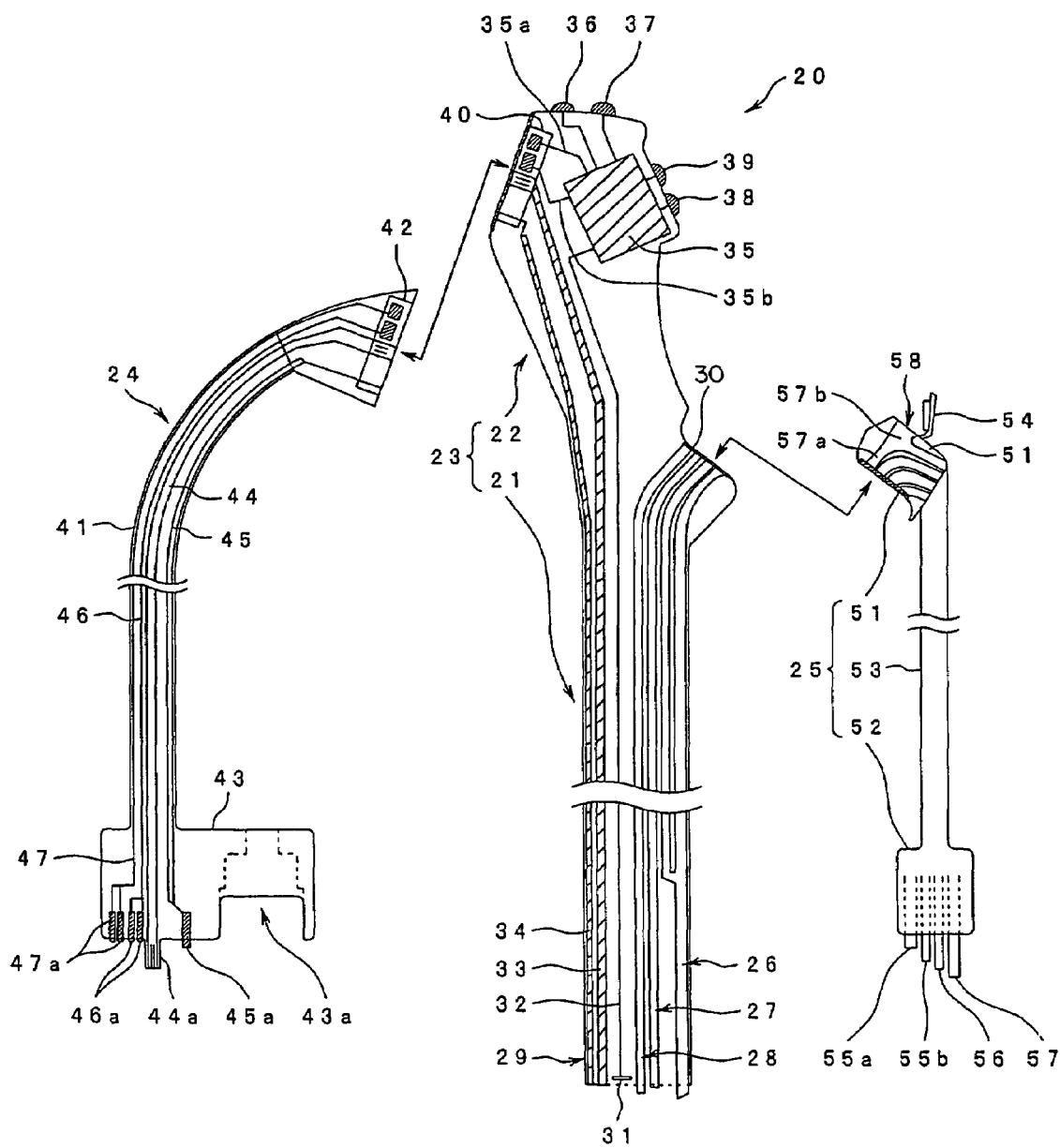
FIG. 5 is a diagram showing a state in which the endoscope is separated to the main-body-portion unit, the universal cord unit, and a channel unit.

First, a description is given of the structure and the operation of a connecting portion A between the main-body-portion unit 23 and the cord unit 24 with reference to FIGS. 3, 4, and 5.

Referring to FIG. 4, the cord connecting portion 40 and the main-body-portion connecting portion 42 forming the connecting portion A comprise: power supply transmitting portions 40a and 42a which supply power; signal transmitting portions 40b and 42b which transmit electric signals such as video signals; illumination light transmitting portions 40c and 42c which transmit illumination light; and electric wiring connecting portions 40d and 42d serving as earth connecting portions, respectively. The power supply transmitting portions 40a and 42a are formed as non-contact power transmitting portions, namely, non-contact electromagnetic induction and coupling means using a transformer as transmitting means and the signal transmitting portions 40b and 42b are formed as non-contact signal transmitting portions.

Specifically, the power supply transmitting portion 40a of the cord connecting portion 40 comprises a secondary side 60a forming a transformer T1 which forms the non-contact power transmitting portion for transmitting the power to a power supply circuit 62, including a voltage control IC 61. While, the power supply transmitting portion 42a of the main-body-portion connecting portion 42 comprises a primary side 60b forming a first transformer T1 and a driving circuit unit 63 which is switching-driven by power (voltage) supplied from the power supply terminal 47a.

The signal transmitting portion 40b of the cord connecting portion 40 comprises: a secondary side 60c forming a transformer T2; and a signal transmitting unit 64 on the main body portion which drives the transformer T2. While, the signal transmitting portion 42b of the main-body-portion connecting portion 42 comprises: a primary side 60d forming the transformer T2; and a signal transmitting unit 65 on the cord side which reproduces a signal of the CCD transmitted by the transformer T2, an angle control signal, and various sensor signals and transmits them to the scope connector 43.

The secondary side 60a of the transformer T1 is connected to the power supply circuit 62 including the voltage control IC 61, and is connected to the control unit 35. The signal transmitting unit 64 on the main body portion is also connected to the control unit 35. Further, the primary sides 60b and 60d and the secondary sides 60a and 60c have the insulating structures and waterproof structures.

The illuminating light transmitting portion 40c of the cord connecting portion 40 has an optical connector 66 as optical transmitting means. The illuminating light transmitting portion 42c of the main-body-portion connecting portion 42 has an optical connector 67 as optical transmitting means. Thus, the illuminating light transmitted by the light guide 44 arranged to the cord unit 24 is transmitted to the light guide 33 arranged to the main-body-portion unit 23 via the optical connector 67 and the optical connector 66.

A branching light guide 33a is branched from the light guide 33, and is arranged to the end portion of the cord connecting portion 40 of the light guide 33. An LED 68 is arranged as an auxiliary light source, at a predetermined position on the end surface side of the branching light guide 33a. Thus, the amount of observation light illuminated from the distal portion of the endoscope is caught by the LED 68. The LED 68 is connected to a power supply arranged to the endoscope 20.

An electric contact 69 is arranged to the electric wiring connecting portion 40d of the cord connecting portion 40. The electric wiring connecting portion 42d of the main-body-portion connecting portion 42 has an electric contact 70. Thus, the earth electric wire 45 arranged to the cord unit 24 is electrically connected to the earth electric wire 34 arranged to the main-body-portion unit 23 by the electric contact 69 and the electric contact 70.

The cord connecting portion 40 and the main-body-portion connecting portion 42 has a detachable portion using magnetic force of a magnet, containing a mechanical connecting portion having a resin member or a metallic member.

According to the first embodiment, the cord connecting portion 40 is arranged to the main-body-portion unit 23 and the main-body-portion connecting portion 42 is arranged to the cord unit 24. Thus, as shown in FIGS. 3 and 5, the main-body-portion unit 23 is detachable from the cord unit 24.

Further, the cord connecting portion 40 of the main-body-portion unit 23 and the main-body-portion connecting portion 42 of the cord unit 24 comprise, as electric contacts, the electric wiring connecting portions 40d and 42d for electric knife forming electric connecting portions. In addition, the power supply transmitting portions 40a and 42a and the signal transmitting portions 40b and 42b forming other electric connecting portions are formed as the non-contact power transmitting portions and the non-contact signal transmitting portions having the transformers. Consequently, the number of electric contacts in the connecting portions is reduced as much as possible and the resistant quality, e.g., the rust generation which has been the problem for cleaning and sterilizing the endoscope is drastically improved.

Next, a description is given of the structure and the operation of a connecting portion B between the channel unit 25 and the main-body-portion unit 23 with reference to FIGS. 3 and 5.

One end portion of each of the air/water feed channel 26, front water feed sub-channel 27, and suction channel 28 arranged to the main-body-portion unit 23 forming the endoscope 20 is collected to the distal-end portion 29. The other end portion of each of the air/water feed channel 26, front water feed sub-channel 27, and suction channel 28 is collected to the channel unit connecting portion 30 near the boundary between the inserting portion 21 and the operating portion 22. In addition, the air/water feed channel 26, front water feed sub-channel 27, and suction channel 28 extending from the distal-end portion 29 to the channel unit connecting portion 30 exclude, from the halfway portions, a cylinder portion and a bent portion which become a factor for complicating the operability upon cleaning and sterilizing.

The channel unit connecting portion 30 is connected to the first channel-connector portion 51 by one touch. Referring to FIG. 5, the air/water feed channel 26, front water feed sub-channel 27, and suction channel 28 are collected to the main-body-portion unit 23, from which the channel unit 25 is detached, without distribution and with substantially straight line having the dimension shorter than the conventional ones between the distal-end portion 29 and the channel unit connecting portion 30.

That is, according to the first embodiment, the channel unit connecting portion 30 is arranged to the main-body-portion unit 23, and the first channel-connector portion 51 is arranged to the channel unit 25. Thus, referring to FIGS. 3 and 5, the main-body-portion unit 23 is detachable from the channel unit 25.

When the channel unit 25 is detached from the main-body-portion unit 23, the branched portion 26a, channel 26b, front water feed sub-channel 27, and suction channel 28, which are substantially straight, without the cylinder portion are collected to the main-body-portion unit 23, thereby easily, fast, and assuredly cleaning and sterilizing the branched portion 26a, channel 26b, front water feed sub-channel 27, and suction channel 28.

Figure 6:
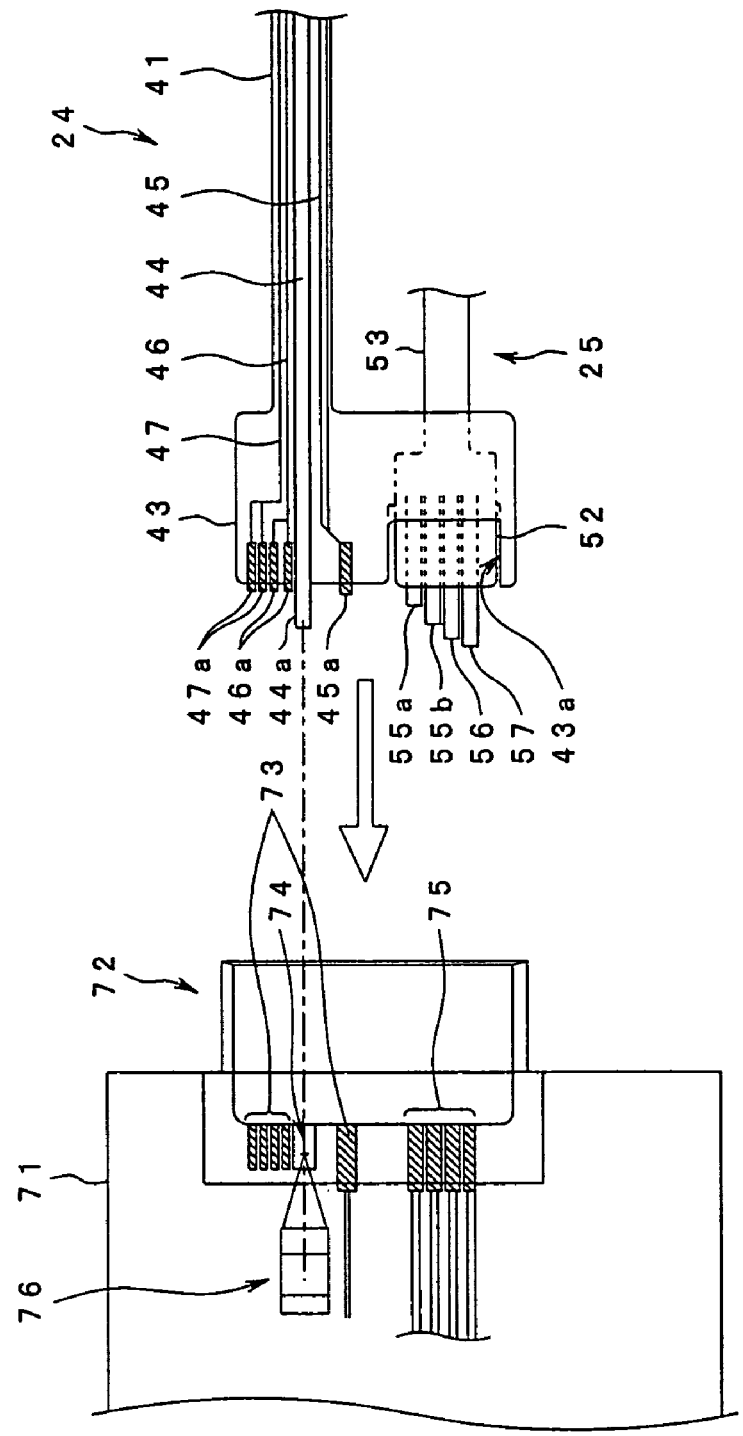
FIG. 6 is a diagram for explaining the structure of a connecting portion between an electric system, optical system, and channel system of a scope connector and an electric system, optical system, and channel system of a multi-connector.
Figure 7:
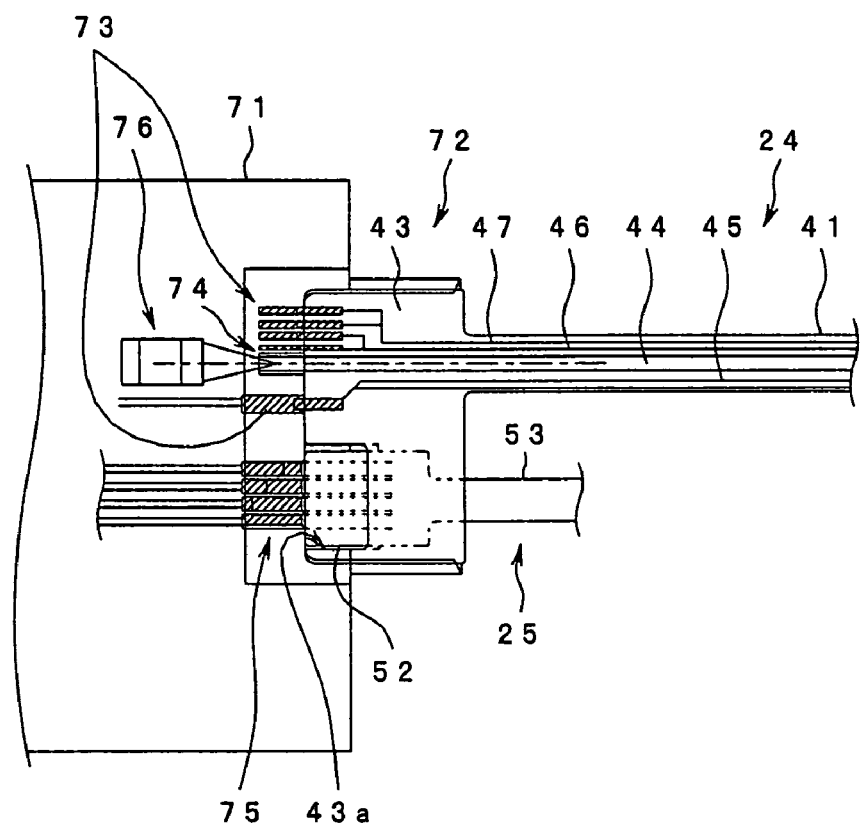
FIG. 7 is a diagram showing a state in which the scope connector is connected to the multi-connector.

Next, a description is given of the structure and the operation of a connecting portion C between the scope connector 43 having the second channel-connector portion 52 and the multi-connector 72 of the endoscope control device 71 with reference to FIGS. 3, 6, and 7.

Referring to FIGS. 3 and 6, the scope connector 43 comprises: the power supply terminal 47a, signal transfer terminal 46a, and E terminal 45a as the connecting portions of the electric system; and the light guide connector 44a as the connecting portion of the optical system. The connector arranging portion 43a comprises the second channel-connector portion 52 of the channel unit 25 as a connecting portion of the channel system.

The power supply terminal 47a is a terminal for supplying power from the endoscope control device 71 to the endoscope 20 side. The signal transfer terminal 46a is a terminal for transmitting, between the main-body-portion unit 23 and the endoscope control device 71, the signal from the CCD 31, angle control signal, and various sensor signals. The light guide connector 44a is a connector which introduces, to the endoscope 20, the observation light used upon the observation supplied from the endoscope control device 71. The E terminal 45a is a terminal to which the earth for electric knife is connected.

While, the scope connector 43 with the above structure is connected to the multi-connector 72 of the endoscope control device 71. Referring to FIG. 6, the multi-connector 72 comprises: an electric system connector 73 as the connecting portion of the electric system; an optical system connector 74 as the connecting portion of the optical system and a channel system connector 75 as the connecting portion of the channel system.

The power supply terminal 47a, signal transfer terminal 46a, and E terminal 45a are electrically connected to the electric system connector 73. The light guide connector 44a is connected to the optical system connector 74. The first channel 55a, second channel 55b, third channel 56, and fourth channel 57, which are arranged to the second channel-connector portion 52, are connected to the channel system connector 75.

Reference numeral 76 denotes a light source device. A lamp (not shown), a condense lens (not shown), and a stop (not shown) are arranged to the light source device 76. Illuminating light generated by the lamp passes through the condense lens and the stop and then is condensed to a predetermined position of the optical system connector 74.

The scope connector 43 with the above structure is brought closer to the multi-connector 72 of the endoscope control device 71 as shown by an arrow. Further, the scope connector 43 is pressed into the multi-connector 72. Then, referring to FIG. 7, the scope connector 43 is connected to the multi-connector 72 by one touch operation. In this connecting state, the signal transfer terminal 46a, the power supply terminal 47a and the E terminal 45a are electrically connected to the electric system connectors 73, respectively. The optical system connector 74 is connected to the light guide connector 44a in a predetermined state. Further, the first channel 55a, second channel 55b, third channel 56, and fourth channel 57 are communicated with the channel system connector 75.

That is, the scope connector 43 is connected to the multi-connector 72, and the electric system, optical system, and channel system of the endoscope control device 71 are easily and simultaneously connected to the electric system, optical system, and channel system of the endoscope 20. As a consequence, the operability is improved by omitting the operation for connecting the channels and the operation for connecting the electric connector according to the conventional endoscope system.

The structure of the endoscope control device 71 will be described with reference to FIG. 8.

Figure 8:
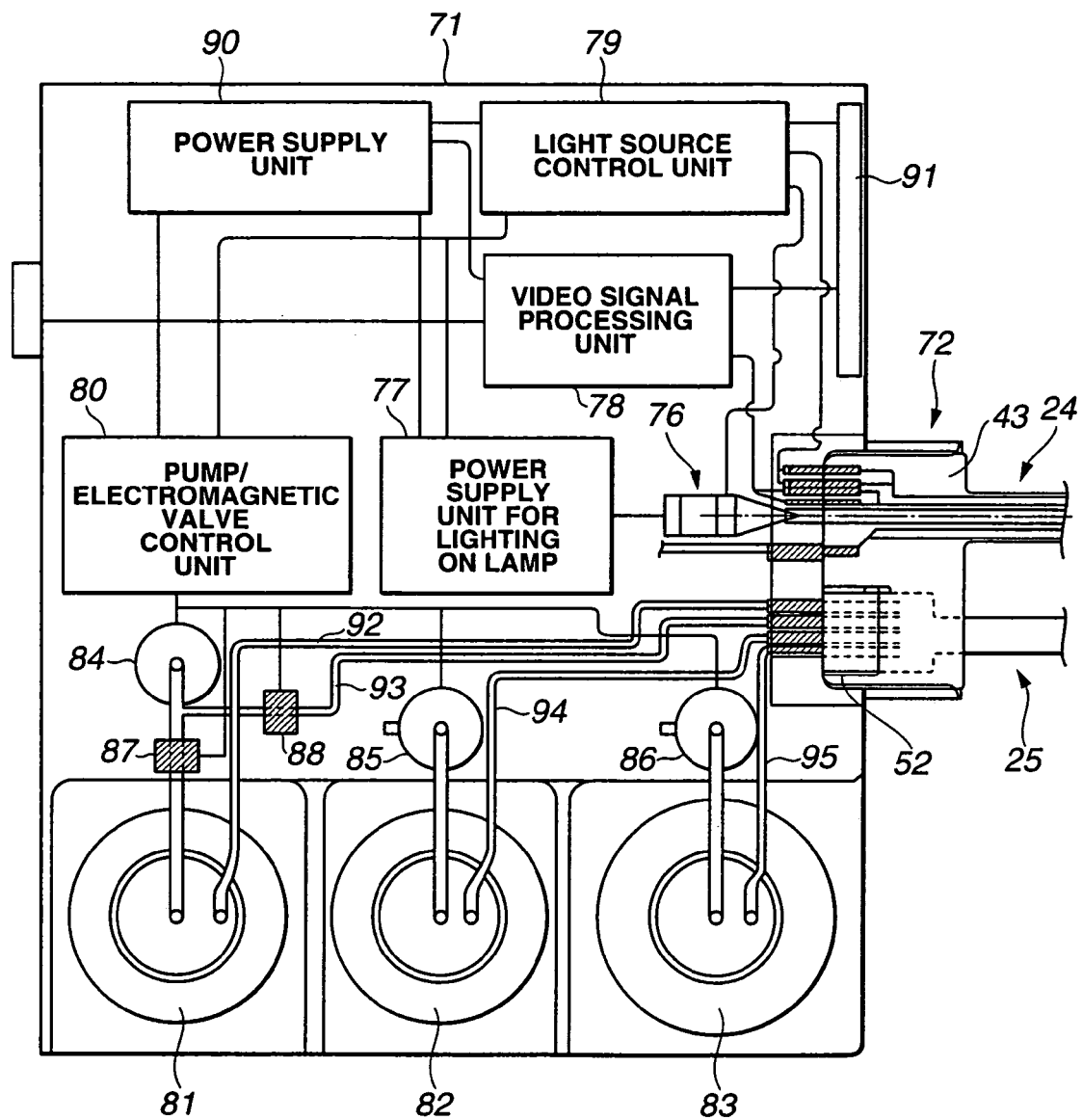
FIG. 8 is a diagram for explaining the structure of an endoscope control device.

Referring to FIG. 8, the endoscope control device 71 comprises: the light source device 76; a power supply unit 77 for lighting-on a lamp; a video signal processing unit 78; a light source control unit 79; a pump/electromagnetic valve control unit 80; an air/water feed bottle 81; a sub water-feed bottle 82; a suction bottle 83; an air/water feed pump 84; a sub water-feed pump 85; a suction pump 86; a water feed electromagnetic valve 87; an air feed electromagnetic valve 88; and a power supply unit 90. Reference numeral 91 denotes a panel control unit. Reference numeral 92 denotes a water feed channel in the apparatus. Reference numeral 93 denotes an air feed channel in the apparatus. Reference numeral 94 denotes a sub water-feed channel in the apparatus. Reference numeral 95 denotes a suction channel in the apparatus.

The power supply unit 77 for lighting-on the lamp controls the light-on state of the lamp arranged to the light source device 76. The video signal processing unit 78 performs and controls various signals corresponding to the control unit 35. The light source control unit 79 controls a stop control unit (not shown) based on an output signal from the video signal processing unit 78 and the power supply unit 77 for lighting-on the lamp, further automatically controls the light adjustment as the brightness adjustment of the observation light, and supplies power to the endoscope 20.

The pump/electromagnetic valve control unit 80 is electrically connected to the air/water feed pump 84, sub water-feed pump 85, and suction pump 86, and the water feed electromagnetic valve 87 and air feed electromagnetic valve 88, and directly controls them so as to operate the air/water feed, suction, and sub water-feed in accordance with the operation of the air/water feed switch 38 and the suction switch 39. Therefore, the channels for the air/water feed, suction, and sub water-feed have the simple structures without arranging the cylinder of the conventional endoscope.

The power supply unit 90 entirely supplies the power to the pump/electromagnetic valve control unit 80, light source control unit 79, video signal processing unit 78, power supply unit 77 for lighting-on the lamp, and the like. The panel control unit 91 controls the panel for display and setting (not shown), which is arrange to the endoscope control device 71. The panel control unit 91 is connected to the light source control unit 79 and the video signal processing unit 78, thereby controlling the entire apparatus.

The air/water feed pump 84 is connected to the air/water feed bottle 81. The sub water-feed pump 85 is connected to the sub water-feed bottle 82. The suction pump 86 is connected to the suction bottle 83. The water feed electromagnetic valve 87 and the air feed electromagnetic valve 88 are arranged among the air/water feed pump 84, the air/water feed bottle 81, and the second channel-connector portion 52.

Next, a description is given of the operation of the endoscope system 100 with the above-mentioned structure.

First, upon performing the endoscope examination with the endoscope system 100, as a preparation, the first channel-connector portion 51 of the channel unit 25 is connected to the channel unit connecting portion 30 of the main-body-portion unit 23. Thus, the first channel 55a, second channel 55b, third channel 56, and the fourth channel 57 of the channel unit 25 are communicated with the branched portion 26a, channel 26b, the front water feed sub-channel 27, and suction channel 28 of the main-body-portion unit 23 in a predetermined state.

The main-body-portion connecting portion 42 of the cord unit 24 is connected to the cord connecting portion 40 of the main-body-portion unit 23. Thus, the non-contact power transmitting portion having the transformer T1 transmits power, the non-contact signal transmitting portion having the transformer T2 transmits the signal, the illuminating light transmitted by the light guide 44 is transmitted to the light guide 33 via the optical connector 67 and the optical connector 66, and the earth electric wire 45 and the earth electric wire 34 are electrically connected to each other by the electric contact 69 and the electric contact 70.

Further, the second channel-connector portion 52 of the channel unit 25 is attached to the connector arranging portion 43a arranged to the scope connector 43 forming the cord unit 24. A series of operation ends and then the endoscope 20 is structured.

Next, the scope connector 43 of the endoscope 20 is connected to the multi-connector 72 of the endoscope control device 71. By connecting the scope connector 43 to the multi-connector 72 by one touch operation, the electric system, the optical system, and the channel system of the endoscope control device 71 are connected to the electric system, the optical system, and the channel system of the endoscope 20 by a single connecting operation. This one-time connection ends and then the set-up operation of the endoscope system 100 completes.

Next, the power of the endoscope control device 71 is turned on so as to start the endoscope examination. Then, the light source control unit 79 for supplying the power to the endoscope 20 operates the driving circuit unit 63 in the cord unit 24. Thus, the voltage control IC 61 in the main-body-portion unit 23 is operated via the insulated transformer T1, and the power is supplied.

The signal is transmitted by the magnetic field or radio waves, thereby operating the control unit 35 in the endoscope 20. Then, the CCD 31 is driven. A CCD driving signal is transmitted to the signal transmitting unit 64 on the main body portion via the control unit 35, and the CCD driving signal is converted into a video signal in the signal transmitting unit 64 on the main body portion. Further, an A/D converter arranged in the signal transmitting unit 64 on the main body portion converts an analog signal into a digital signal.

The digital signal is transmitted to the signal transmitting unit 65 on the cord side in the cord unit 24, via the insulating transformer T2, by the magnetic field or radio waves. After that, the digital signal is transmitted to the video signal processing unit 78 via the signal transfer terminal 46*a* of the scope connector 43 and the electric system connector 73 arranged to the multi-connector 72 of the endoscope control device 71, and then a predetermined signal is generated. The generated video signal is outputted to a display device (not shown) connected to the video signal processing unit 78, thereby displaying an endoscope observed image on a screen and performing the endoscope observation.

The transmitted signal is not limited to the digital signal after the A/D conversion, and an analog signal may be transmitted. The signal processing for converting the CCD driving signal into the video signal may be performed, not by the signal transmitting unit 64 on the main body portion but by the signal transmitting unit 65 on the cord side.

The power is supplied and the control unit 35 is operated and then the zoom switch 36, freeze switch 37, air/water feed switch 38, and suction switch 39 arranged to the main-body-portion unit 23 are operated, thus to transmit, to the endoscope control device 71, signal for instructing various functions such as the air/water feed, (sub) front water-feed, suction, zooming observation, and image freezing.

In addition, the control unit 35 is operated and thus the LED 68 is lit on. Then, the illuminating light necessary for the endoscope observation is auxiliarily supplied. Therefore, even if the lamp of the light source device 76 in the endoscope control device 71 does not light on due to the life or the like, the observation of the endoscope image can be continued.

Next, a description is given of the cleaning and sterilization of the endoscope 20 after ending the endoscope examination.

After ending the endoscope examination, the power of the endoscope control device 71 is turned off. The endoscope control device 71 is separated from the endoscope 20. That is, the scope connector 43 is detached from the multi-connector 72.

Next, the second channel-connector portion 52 of the channel unit 25 is detached from the connector arranging portion 43*a* of the scope connector 43. The first channel-connector portion 51 of the channel unit 25 is detached from the channel unit connecting portion 30 of the main-body-portion unit 23. That is, the channel unit 25 is separated from the main-body-portion unit 23 and the cord unit 24. Then, the separated channel unit 25 is disposed. As a consequence, the channel of the channel unit 25 does not need to be cleaned and be sterilized.

The main-body-portion connecting portion 42 of the cord unit 24 is detached from the cord connecting portion 40 of the main-body-portion unit 23. Thus, the cord unit 24 is separated from the main-body-portion unit 23. The cord unit 24 does not have channels such as the air feed channel. Therefore, only the outer surface of the cord unit 24 need to be cleaned and sterilized. The cord unit 24 according to the first embodiment has extremely small number of electric contacts, as compared with the conventional endoscope. The influence on the resistance against the medical solution and the like upon cleaning and sterilization is minimized. Specifically, the conventional electric endoscope has 20 or more electric contacts of the scope connector. In contrast, the number of electric contacts is 5 and thus it is drastically reduced to ¼ or less. The inconvenience upon supplying the power and transmitting the electric signal by the contact state of the electric contacts in the conventional art is remarkably improved.

In addition to the cleaning and sterilization of the outer surface of the main-body-portion unit 23, the branched portion 26*a*, channel 26*b*, front water feed sub-channel 27, and suction channel 28 are cleaned and sterilized. In the main-body-portion unit 23, there is only one electric contact at the connecting portion with the cord unit 24, that is the electric contact for the earth. As compared with the channel structure of the conventional endoscope, the inserting portion 21 has shorter dimension and further has the air/water feed channel 26, front water feed sub-channel 27, and suction channel 28, which are substantially straight and from which the cylinder portion is excluded. Since the end portions of the branched portion 26*a*, channel 26*b*, front water feed sub-channel 27, and suction channel 28 are collected to the channel unit connecting portion 30, the cleaning and sterilizing operation is easily and fast performed without fail.

A description is given of the second embodiment of the present invention with reference to FIGS. 9 to 13.

According to the second embodiment, the non-contact power transmitting portion and the non-contact signal transmitting portion shown by the A portion in FIG. 3 according to the first embodiment are applied to an electric-system connector arranged to a multi-connector 172 of the endoscope control device 71 and an electric-system connecting portion of a scope connector 143 of the cord unit 24.

Figure 9:
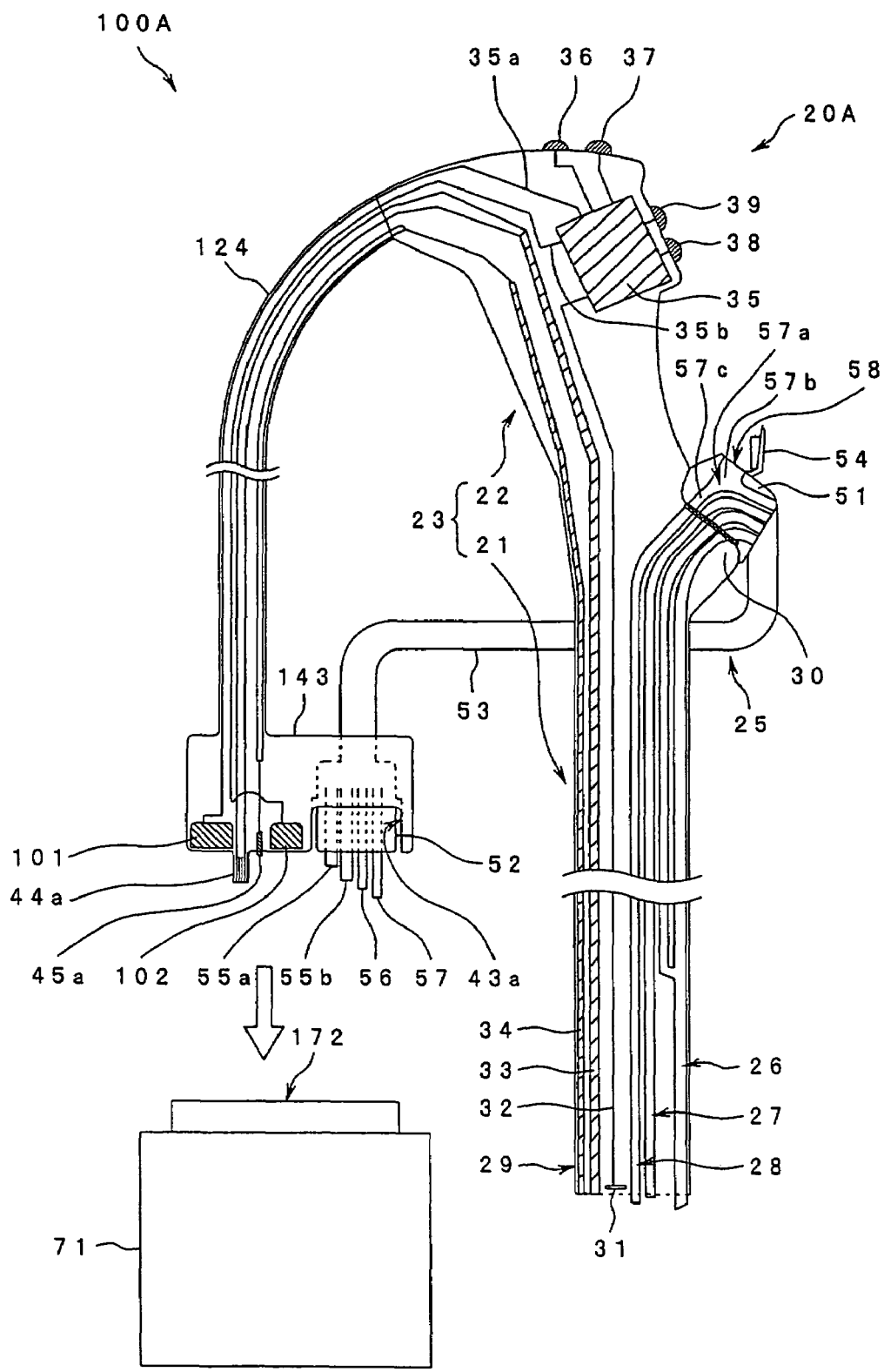
FIG. 9 is a diagram for explaining the structure of an endoscope system according to the second embodiment of the present invention.

Referring to FIG. 9, an endoscope 20A according to the second embodiment is formed by integrating the cord unit 24 and the main-body-portion unit 23. According to the second embodiment, a portion corresponding to the cord unit 24 is referred to as a universal cord 124, into which the light guide 33 extended from the main-body-portion unit 23, earth electric wire 34, and signal lines 35*a* and 35*b* are inserted. Therefore, the endoscope 20A according to the second embodiment comprises: the main-body-portion unit 23 from which the universal cord 124 is extended and the channel unit 25. Other structures are the same as those according to the first embodiment, the same components are designated by the same reference numerals, and a description is omitted.

A specific description is given of the configuration of the scope connector 143 and the multi-connector 172 according to the second embodiment.

Figure 10:
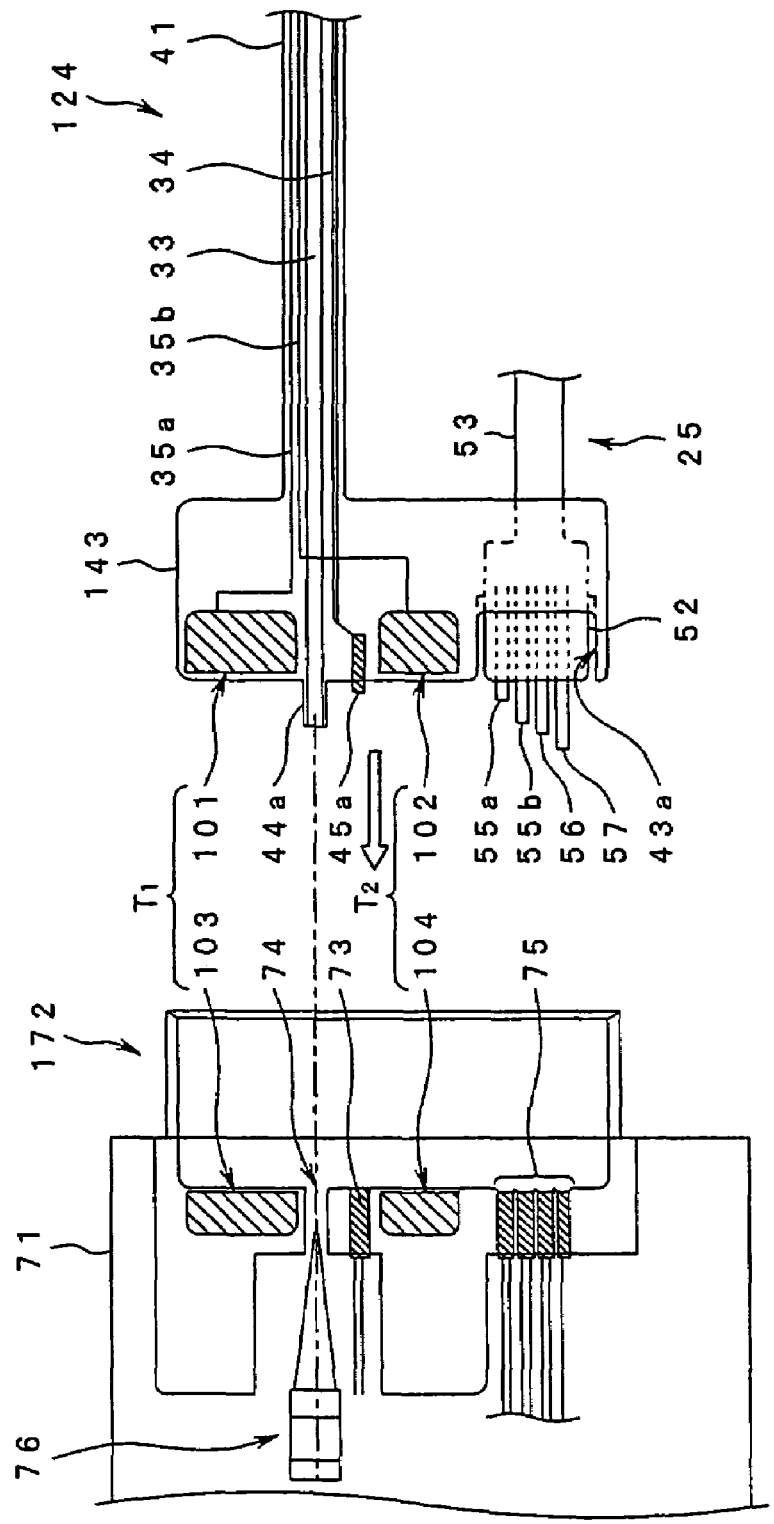
FIG. 10 is a diagram showing the structure of the connecting portion between the electric system, optical system, and channel system of the scope connector and the electric system, optical system, and channel system of the multi-connector.

Referring to FIGS. 9 and 10, the scope connector 143 comprises: a secondary coil 101 forming the transformer T1 for transmitting the power supply; a secondary coil 102 forming the transformer T2 for transmitting the video signal; the E terminal 45*a*; and the light guide connector 44*a*.

Meanwhile, referring to FIG. 10, the multi-connector 172 of the endoscope control device 71 comprises: a primary coil 103 forming the transformer T1; a primary coil 104 forming the transformer T2; the electric system connector 73; the optical system connector 74; and the channel system connector 75.

Figure 11:
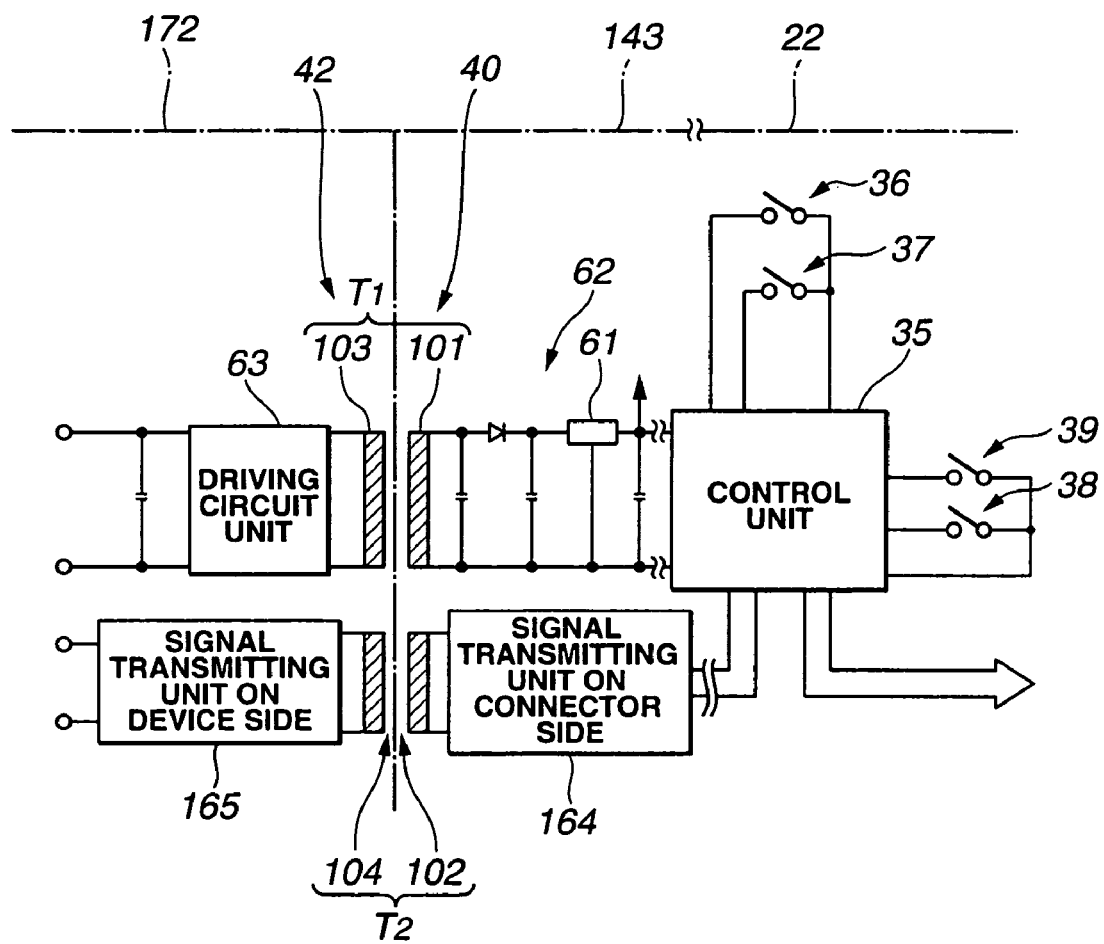
FIG. 11 is a block diagram for explaining the connecting portion between the electric system of the scope connector and the electric system of the multi-connector.

Referring to FIG. 11, the power supply circuit 62 including the voltage control IC 61 is arranged to the secondary coil 101 side of the transformer T1 formed to the scope connector 143. The primary coil 103 side of the transformer T1 comprises the driving circuit unit 63 which drives the switching operation of the primary coil 103 for supplying the power from the endoscope control device 71 to the power supply circuit 62 including the voltage control IC 61.

Meanwhile, the secondary coil 102 side of the transformer T2 comprises a signal transmitting unit 164 on the connector side for driving the transformer T2, and the primary coil 104 side comprises a signal transmitting unit 165 on the device side which reproduces the CCD signal transmitted by the transformer T2, the angle control signal, and various sensor signals, and transmits them to the video signal processing unit 78.

Figure 12:
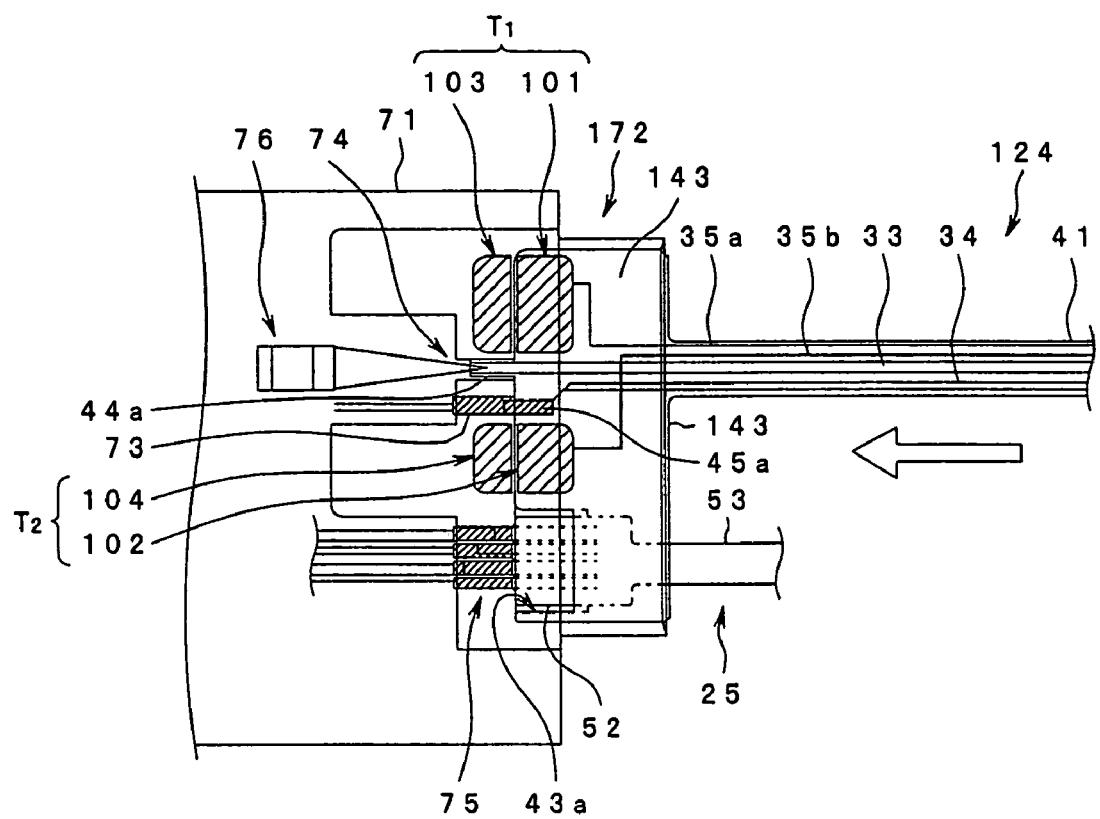
FIG. 12 is a diagram showing a state in which the scope connector is connected to the multi-connector.

In the scope connector 143 with the above-mentioned structure, the scope connector 143 is pushed in the multi-connector 172, thereby connecting the scope connector 143 to the multi-connector 172 by one touch as shown in FIG. 12. In this case, at the same time, the electric system, the optical system, and the channel system of the endoscope control device 71 are connected to the electric system, the optical system, and the channel system of the endoscope 20A.

The power supply circuit 62 and the signal transmitting unit 164 on the connector side are connected to the control unit 35 arranged near the operating portion 22 of the main-body-portion unit 23.

Figure 13:
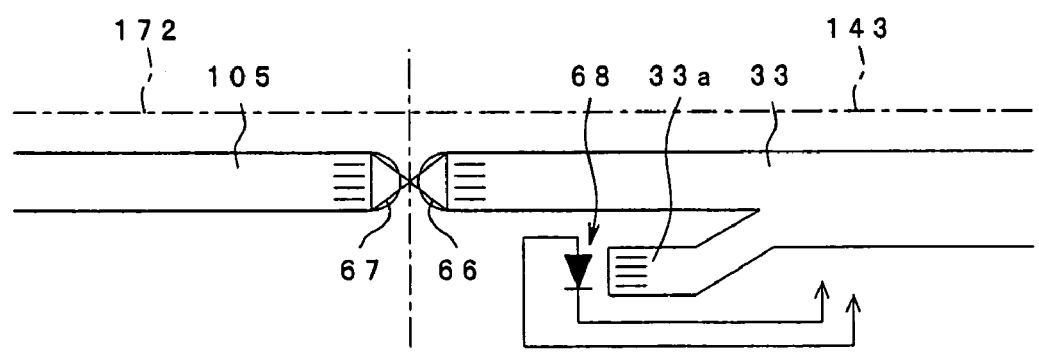
FIG. 13 is a diagram for explaining the structure of the connecting portion of the optical system of the scope connector and the optical system of the multi-connector.

In place of condensing the illuminating light from the light source device 76 to the end surface of the light guide connector 44a as shown in FIGS. 9 and 10, the light guide 105 as the optical transmitting means of the illuminating light transmits the illuminating light from the light source device 76 as shown in FIG. 13, and the optical connectors 66 and 67 transmit the transmitted illuminating light to the light guide 33. As mentioned above, the multi-connector 172 and the scope connector 143 may be structured.

In addition, the branching light guide 33a branched from the light guide 33 is arranged in the scope connector 143. The LED 68 may be arranged to the end surface of the branching light guide 33a, as an auxiliary light source which covers the amount of observation light illuminated from the distal portion of the endoscope. The LED 68 is connected to the power supply arranged to the endoscope 20A.

Next, a description is given of the operation of an endoscope system 100A comprising an endoscope 20A having the scope connector 143 and the endoscope control device 71 having the multi-connector 172 as mentioned above.

Similarly to the first embodiment, as the preparation of the endoscope examination, the first channel-connector portion 51 of the channel unit 25 is connected to the channel unit connecting portion 30 of the main-body-portion unit 23. The second channel-connector portion 52 of the channel unit 25 is attached to the connector arranging portion 43a arranged to the scope connector 143 forming the cord unit 24. A series of operations ends and thus the endoscope 20A is structured.

Next, the scope connector 143 of the endoscope 20A is connected to the multi-connector 172 of the endoscope control device 71. Then, the non-contact power transmitting portion having the transformer T1 enables the power transmission, the non-contact signal transmitting portion having the transformer T2 enables the signal transmission, and the electric system connector 73, optical system connector 74, and channel system connector 75 of the endoscope control device 71 are connected to the E terminal 45a, light guide connector 44a, the first channel 55a, second channel 55b, third channel 56, and fourth channel 57 of the endoscope 20. That is, the multi-connector 172 is connected to the scope connector 143 by a single operation, then, the electric systems, optical systems, and channel systems are connected, and the set-up operation of the endoscope system 100A completes.

Next, the power supply of the endoscope control device 71 is turned on. Then, the light source control unit 79 for supplying the power to the endoscope 20 operates the driving circuit unit 63 in the apparatus, the voltage control IC 61 in the scope connector 143 is operated via the insulated transformer T1, the power is supplied to the endoscope 20A. The control unit 35 in the endoscope 20 is operated, thus, the CCD 31 is driven, and the CCD driving signal is transmitted to the signal transmitting unit 164 on the connector side via the control unit 35.

The CCD driving signal is converted into the video signal in the signal transmitting unit 164 on the connector side. Further, the video signal is converted into a digital signal by an A/D converter arranged to the signal transmitting unit 164 on the connector side. The digital signal is transmitted to the signal transmitting unit 165 on the device side via the insulated transformer T2 by the magnetic field or radio waves, then, the signal is transmitted to the video signal processing unit 78 in the endoscope control device 71, and the endoscope observation is performed.

A description is given of the cleaning and sterilization of the endoscope after ending the endoscope examination.

After ending the endoscope examination, the power of the endoscope control device 71 is turned off. The endoscope control device 71 is separated from the endoscope 20. That is, the scope connector 43 is detached from the multi-connector 72. The second channel-connector portion 52 of the channel unit 25 is detached from the connector arranging portion 43a of the scope connector 43. Further, the first channel-connector portion 51 of the channel unit 25 is detached from the channel unit connecting portion 30 of the main-body-portion unit 23. That is, the channel unit 25 is separated from the main-body-portion unit 23 and the cord unit 24. The separated channel unit 25 is disposed.

According to the second embodiment, the main-body-portion unit 23 from which the universal cord 124 is extended is cleaned and sterilized. In this case, the universal cord 124, the outer surface of the main-body-portion unit 23, the branched portion 26a, channel 26b, front water feed sub-channel 27, and suction channel 28 are cleaned and sterilized.

As compared with the conventional endoscope, the universal cord 124 has the extremely small number of electric contacts. Specifically, the conventional electric endoscope has 20 or more electric contacts. The electric endoscope according to the second embodiment has only one electric contact which is 1/20 or less of electric contacts of the conventional endoscope. Thus, the influence on the resistance due to the medical solution upon cleaning and sterilization is further minimized. Other operations and advantages are the same as those according to the first embodiment.

Needless to say, the endoscope may be structured by combining the first embodiment and the second embodiment.

The third embodiment of the present invention will be described with reference to FIGS. 14 to 16.

According to the third embodiment, the connecting portion between the E terminal 45a of the scope connector 143 and the electric system connector 73 of the multi-connector 172 is different from that shown in FIGS. 9 and 10 according to the second embodiment.

A description is given of the configuration of a scope connector 243 and a multi-connector 272 according to third embodiment.

Figure 14:
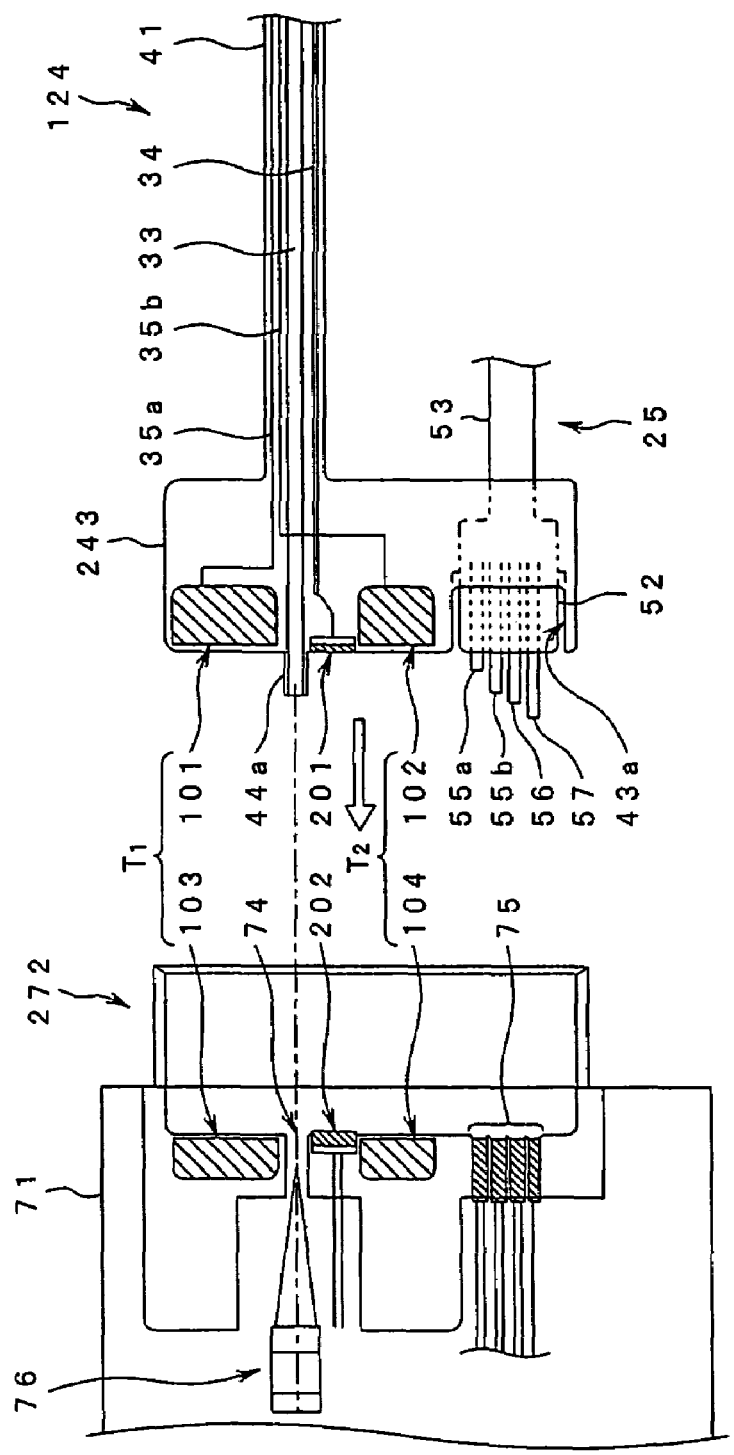
FIG. 14 is a diagram for explaining another structure of the scope connector and the multi-connector.

Referring to FIG. 14, the scope connector 243 comprises: the secondary coils 101 and 102; the light guide connector 44a; and an electric connecting portion 201 on the endoscope side as high-frequency connecting means. Meanwhile, the multi-connector 272 comprises: the primary coils 103 and 104; the optical system connector 74; and an electric connecting portion 202 on the device side as the high-frequency connecting means.

Figure 15:
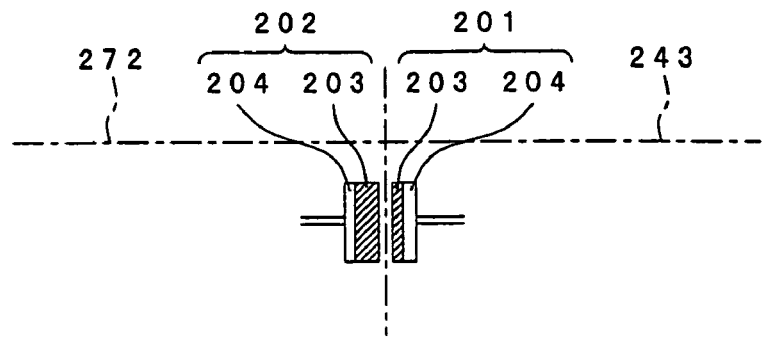
FIG. 15 is a diagram for explaining the structure of high-frequency connecting means which connects an electric knife to the earth.

Referring to FIG. 15, the electric connecting portion 201 on the endoscope side and the electric connecting portion 202 on the device side have the same function as that of the capacitor by arranging a dielectric member 203 to a conductive member 204 such as a metallic member. The electric connecting portion 201 on the endoscope side and the electric connecting portion 202 on the device side comprise the conductive member 204 and the dielectric member 203, and the electric connecting portion 201 on the endoscope side is insulated to the electric connecting portion 202 on the device side in a direct current manner. Further, the electric connecting portion 201 on the endoscope side and the electric connecting portion 202 on the device side are arranged to a multi-connector 272 and the scope connector 243 with the waterproof structure.

Figure 16:
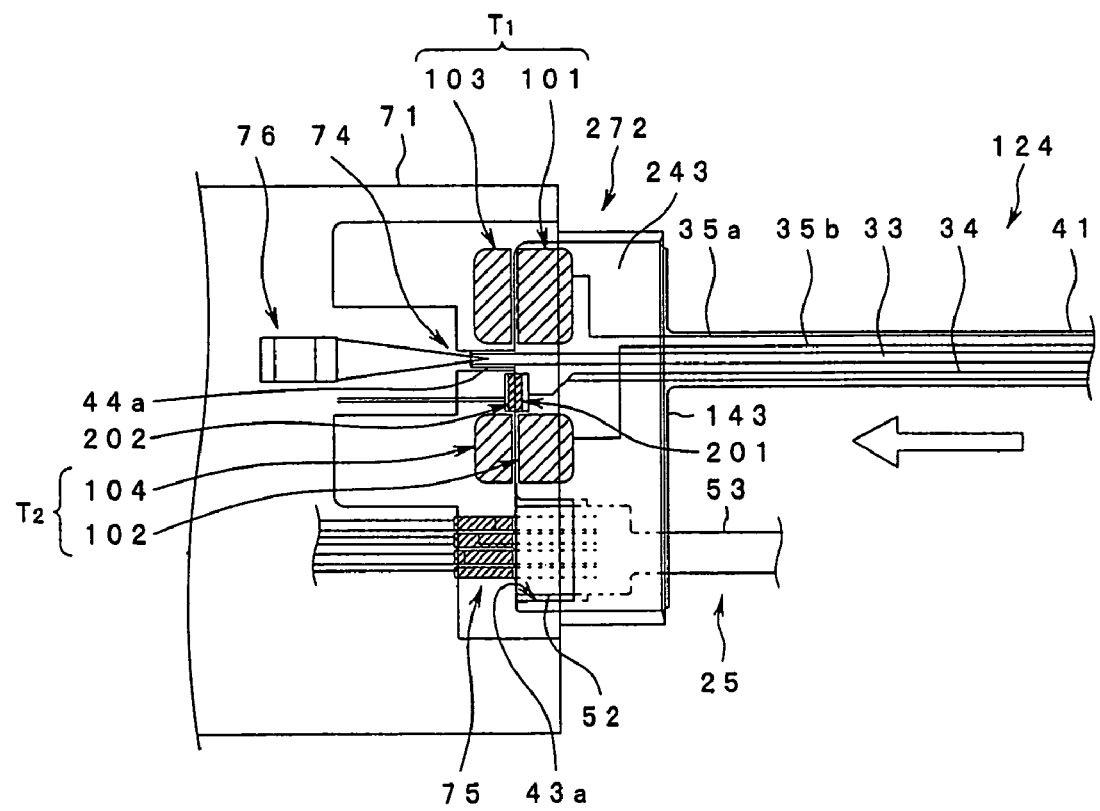
FIG. 16 is a diagram showing a connecting state of another structure of the scope connector and the multi-connector.

The scope connector 243 with the above-mentioned structure is pressed in the multi-connector 272, thereby connecting the scope connector 243 to the multi-connector 272 by one touch as shown in FIG. 16. In this case, at the same time, the electric system, optical system, and channel system of the endoscope control device 71 are connected to the electric system, optical system, and channel system of the endoscope 20A.

Generally, the output frequency of the electric knife is 350 KHz or more, and has sufficiently low impedance from the viewpoint of high-frequency in the capacitor structure having the conductive member 204 and the dielectric member 203 in the electrically connecting state shown in FIG. 16. Therefore, the electric connecting portion 201 on the endoscope side and the electric connecting portion 202 on the device side enable the connection while the electric knife is connected to the earth without any problem.

Other structure is the same as that according to the second embodiment, the same reference numerals denote the same components, and a description thereof is omitted.

In the scope connector 243 with the above-mentioned structure, the electric contact structure is omitted in the universal cord 124 upon cleaning and sterilizing the main-body-portion unit 23 from which the universal cord 124 is extended, and the influence on the resistance due to the medical solution or the like is further suppressed to the minimum.

A description is given of the fourth embodiment of the present invention with reference to FIGS. 17 to 22.

According to the fourth embodiment, the endoscope system has the structure for rotating the electric-system connecting portion and the optical-system connecting portion of the scope connector 243 to the electric-system connecting portion and the optical-system connecting portion of the multi-connector 272 shown in FIGS. 14 and 16 according to third embodiment.

The specific structure will be described according to the fourth embodiment.

Figure 17:
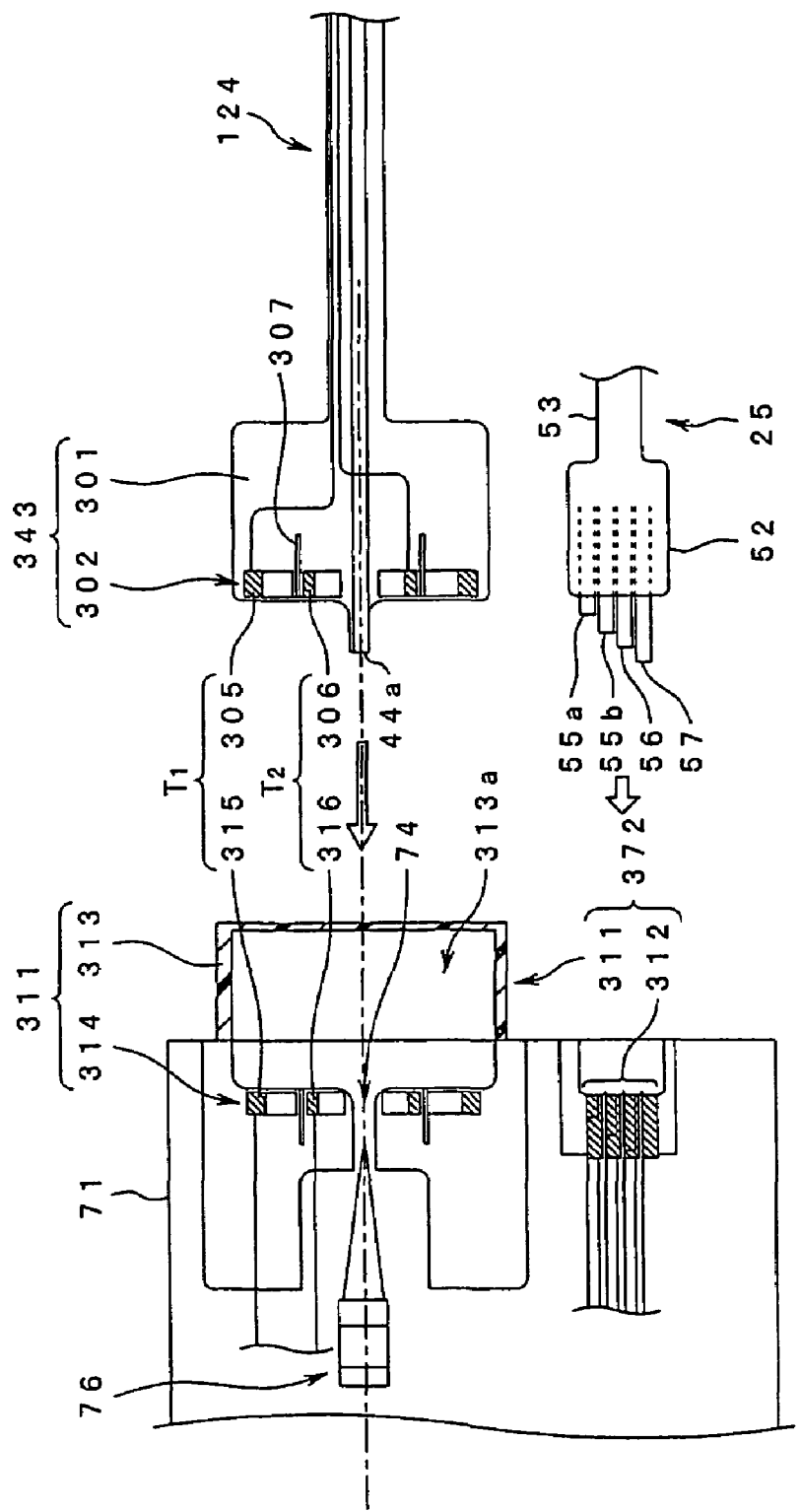
FIG. 17 is a diagram for explaining the structure for rotating the scope connector arranged to the multi-connector portion.
Figure 18:
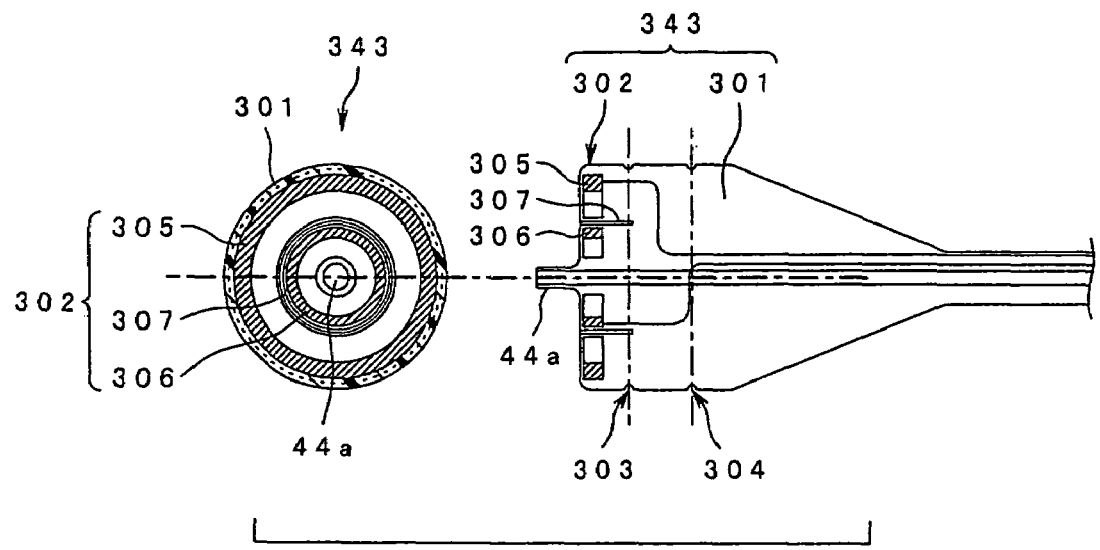
FIG. 18 is a diagram for explaining the structure of the scope connector.

Referring to FIGS. 17 and 18, a scope connector 343 is independent of the second channel-connector portion 52.

The scope connector 343 mainly comprises an exterior member 301 and a disc-shaped member 302. The exterior member 301 contains an insulating member, and the disc-shaped member 302 is arranged at a predetermined position on the distal-end surface side of the exterior member 301. Two peripheral grooves 303 and 304 are formed onto the outer peripheral surface of the exterior member 301.

The light guide connector 44a is arranged in the center of the disc-shaped member 302. The disc-shaped member 302 coaxially comprises: a secondary coil 305 forming the transformer T1; and a secondary coil 306 forming the transformer T2 with the light guide connector 44a as center. An insulating member 307 is arranged to ensure the electric insulation between the transformers T1 and T2. The insulating member 307 has a shielding portion (not shown) to suppress the harmful influence of signals due to the leak of magnetic flux between the transformers T1 and T2. The transformer T1 is for the non-contact power connecting portion, and the transformer T2 is for the non-contact signal transmitting portion.

Figure 19:
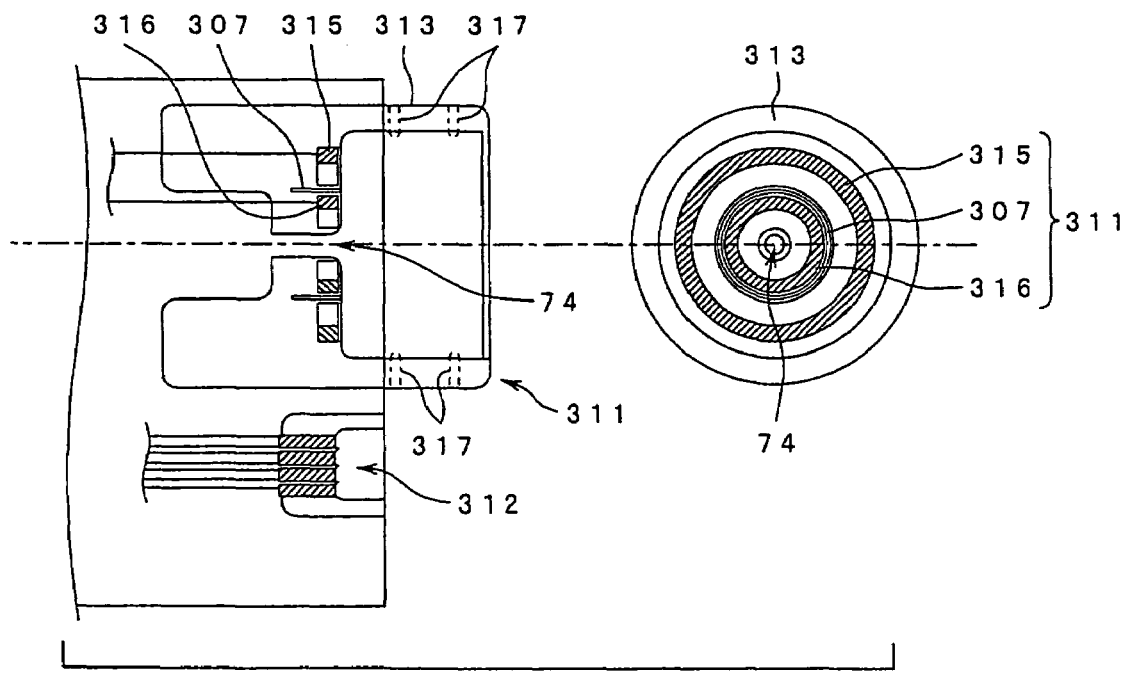
FIG. 19 is a diagram for explaining the structure of the multi-connector portion.

Meanwhile, referring to FIGS. 17 and 19, the endoscope control device 71 comprises a connector portion 372. The connector portion 372 comprises: a multi-connector portion 311 which has the scope connector 343 and which commonly functions as the electric system and the optical system; and a channel-system connector portion 312 having the second channel-connector portion 52.

The multi-connector portion 311 comprises: a cylindrical member 313 forming the exterior portion; and a disc member 314 which is arranged to the bottom of the internal space formed to the cylindrical member 313, corresponding to the disc-shaped member 302. The optical system connector 74 is arranged in the center of the cylindrical member 313, corresponding to the light guide connector 44a.

The scope connector 343 is arranged in an internal space 313a of the cylindrical member 313. The internal space 313a of the cylindrical member 313 is formed so that the scope connector 343 rotates with the light guide connector 44a as center. A plurality of ball plungers 317 are arranged to the internal peripheral surface of the cylindrical member 313. An urging member (not shown) arranged to the ball plunger 317 forces a ball in the central axis direction, and the ball is arranged to the peripheral grooves 303 and 304 of the exterior member 301. That is, the scope connector 343 is pressed in the multi-connector portion 311, thereby rotatably holding the scope connector 343 in the internal space 313a in a predetermined connecting state. The detachable property of the scope connector 343 is preferable.

A primary coil 315 forming the transformer T1 and a primary coil 316 forming the transformer T2 are coaxially arranged to the bottom of the cylindrical member 313 with the optical system connector 74 as center. The insulating member 307 is arranged between the transformer T1 and the transformer T2.

Figure 20:
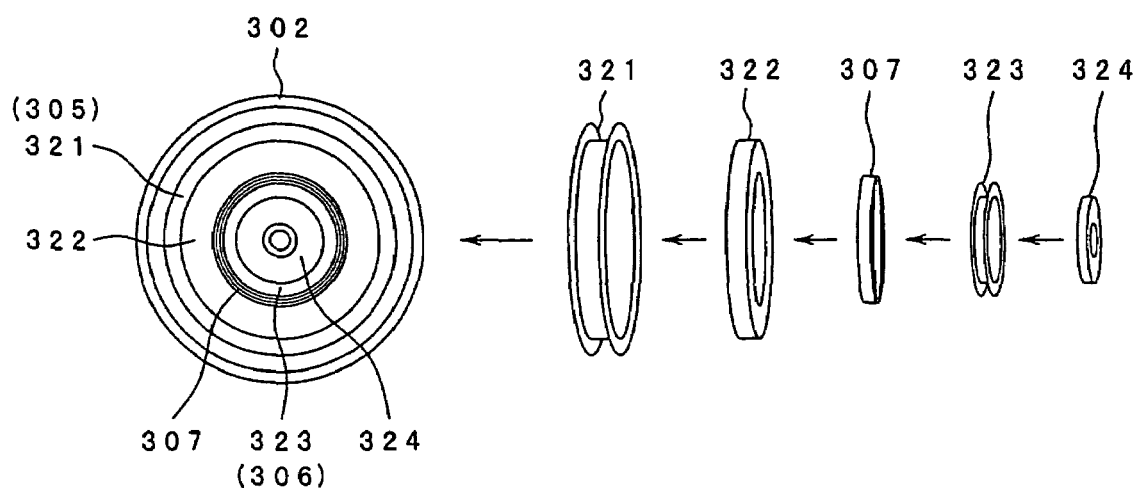
FIG. 20 is a diagram for explaining a structure example of a disc member.

Referring to FIG. 20, the disc-shaped member 302 sequentially has, from the outer peripheral side, a bobbin 321 for structuring the T1 and a core member 322 for the T1 which form the transformer T1, an insulating member 307 including a shielding member, and a bobbin 323 for structuring the T2 and a core member 324 for the T2 which form the transformer T2.

Figure 21:
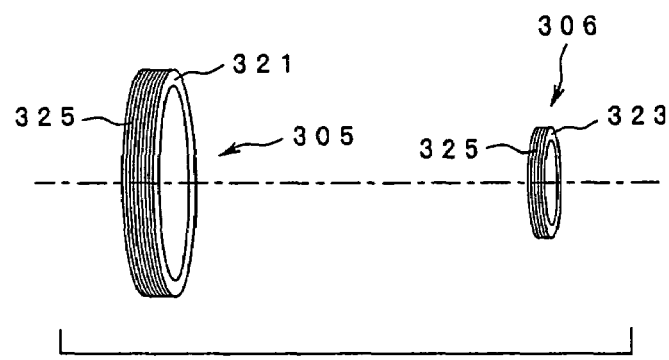
FIG. 21 is a diagram for explaining a structure example of a coil.

Referring to FIG. 21, a coil 325 is wound to the bobbin 321 for structuring the T1 and the bobbin 323 for structuring the T2, and thus the secondary coils 305 and 306 of the transformers T1 and T2 are formed. A filling member (not shown) is injected to the distal-end side portion of the exterior member 301 forming the scope connector 343, thereby assembling the disc-shaped member 302. A cover (not shown) is covered to the distal-end surface in contact with the multi-connector portion 311, and then is subjected to the insulating processing and waterproof processing. Meanwhile, the disc member 314 is assembled to the bottom portion of the cylindrical member 313 forming the multi-connector portion 311 by injecting a filling member (not shown). A cover (not shown) is covered to the surface in contact with the scope connector 343 and the surface is subjected to the insulating processing and the waterproof processing.

Figure 22:
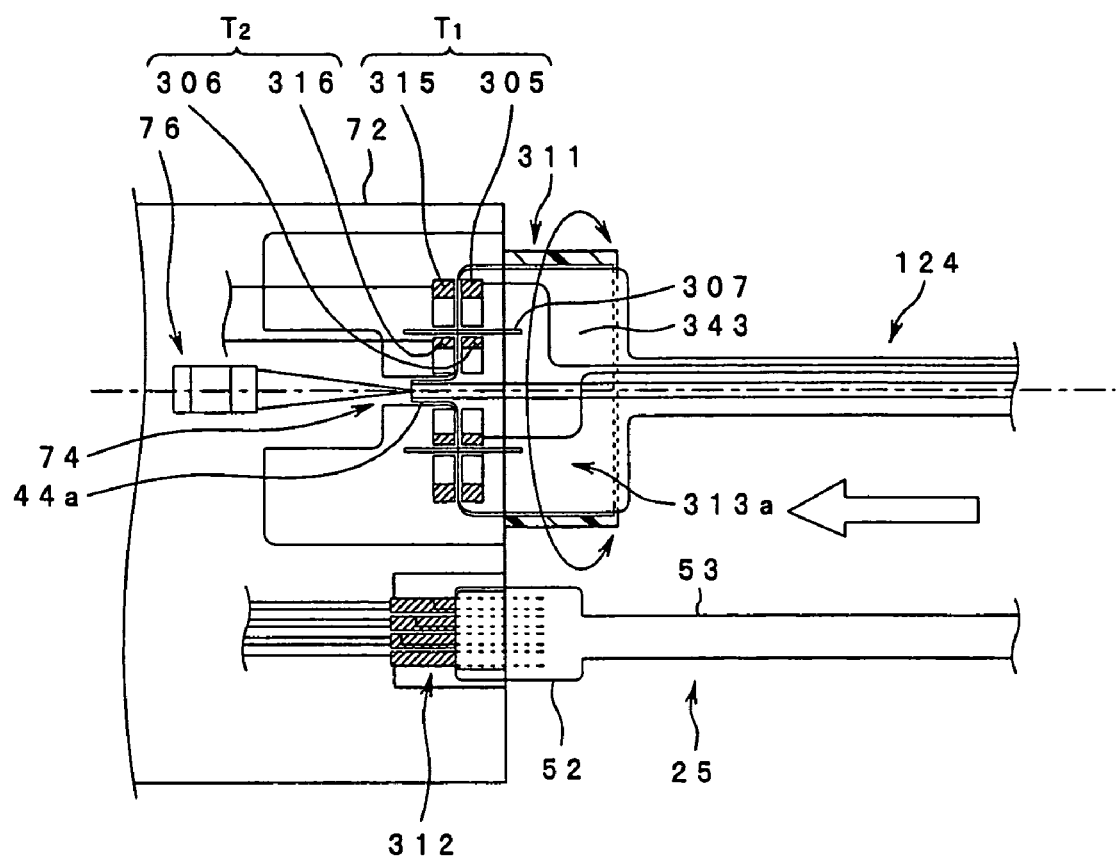
FIG. 22 is a diagram for explaining a rotating state of the scope connector arranged to the multi-connector portion.

According to the fourth embodiment, referring to FIG. 22, the scope connector 343 of the endoscope 20A is connected to the multi-connector portion 311 of the endoscope control device 71, the second channel-connector portion 52 is connected to the channel-system connector portion 312, and the set-up operation of the endoscope system 100A ends.

Even if the scope connector 343 rotates in this state, the power and the electric signal are transmitted by the transformer T1 forming the non-contact power supply connecting portion and the transformer T2 forming the non-contact signal transmitting portion, which are coaxially arranged to the light guide connector 44a and the optical system connector 74, the light guide connector 44a being positioned on the center axis of the scope connector 343 and the optical system connector 74 being positioned on the center axis of the multi-connector portion 311. Therefore, even if the scope connector 343 rotates as shown by an arrow, the scope connector 343 and the multi-connector portion 311 transmit the power and the electric signal without fail.

Therefore, it is possible to realize a technology for rotating the main-body-portion unit 23 in the inserting direction during observation. Thus, in the case of using the endoscope for the examination of the large intestine, the endoscope is assuredly inserted in the large intestine with the complicated shape in a short time while rotating the endoscope main body in the inserting direction during the observation.

The fifth embodiment of the present invention will be described with reference to FIG. 23.

According to the above-mentioned embodiment, the transformer T1 and the transformer T2 are used so as to form the non-contact power transmitting portion and the non-contact signal transmitting portion as means for transmitting the power or electric signal. That is, in order to transmit the power and the electric signal, the two transformers T1 and T2 are arranged in the cord connecting portions 40 and 42. Therefore, there is a problem that the structure of the connecting portion is large.

In order to solve the problem, according to the fifth embodiment, one transformer transmits the power and the electric signal. This is an improvement example which can be applied to the non-contact power transmitting portion and the non-contact signal transmitting portion which are shown according to the first to fourth embodiments.

Figure 23:
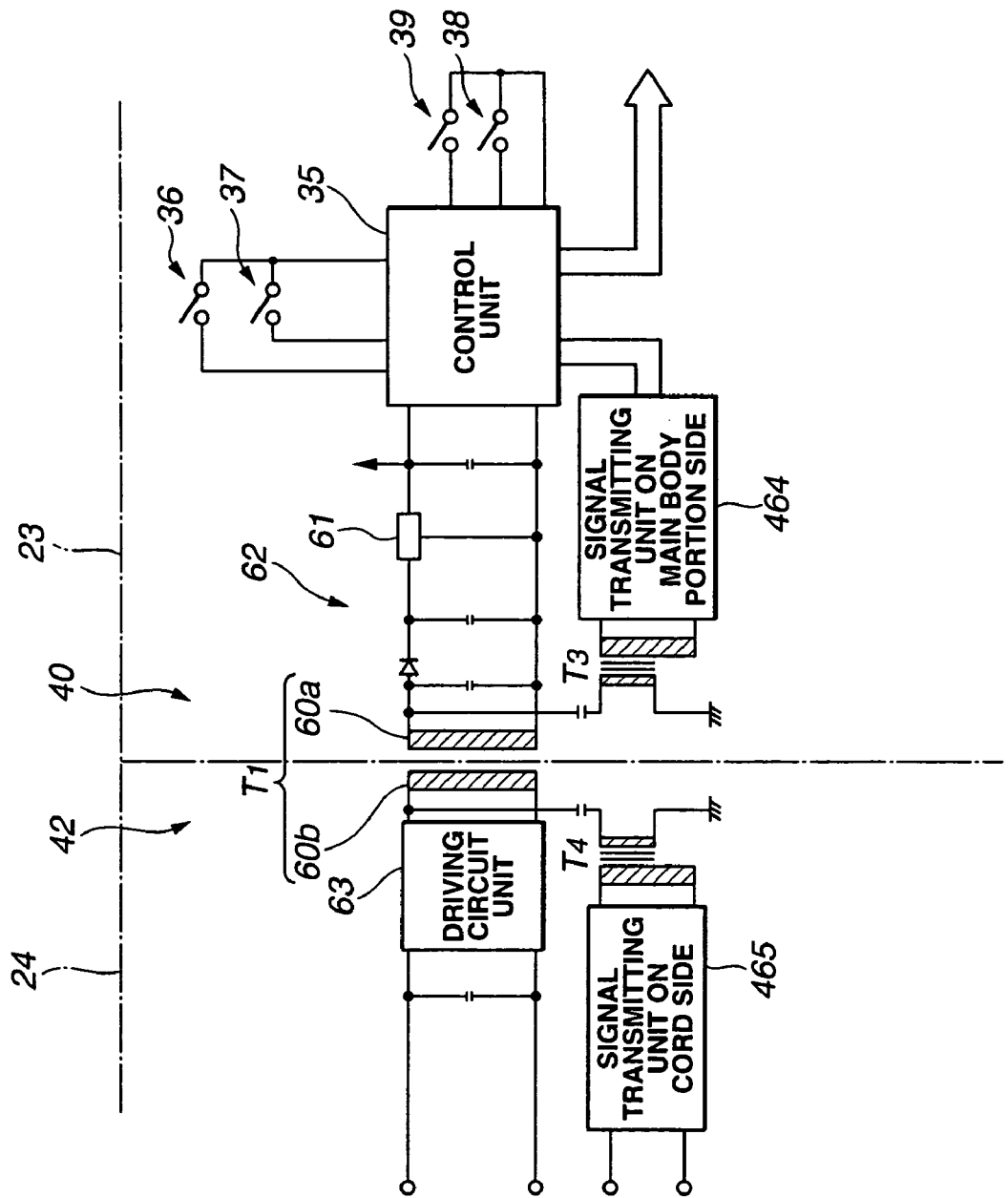
FIG. 23 is a diagram for explaining the structure of non-contact power/signal transmitting portions comprising one transformer.

Referring to FIG. 23, the transmitting route of the power is the same as that according to the first embodiment in the non-contact power and signal transmitting portions according to the fifth embodiment. In contrast, the electric signal such as the video signal is transmitted by using a signal transmitting unit 464 on the main body portion side having a converting transformer T3 and a signal transmitting unit 465 on the cord side having a converting transformer T4. That is, according to the fifth embodiment, upon transmitting the signal, the transmitting signal uses the converting transformers T3 and T4, thereby extracting only the AC and high-frequency component and modulating and transmitting it.

The signal is superimposed to the transformer T1, a modulating circuit and a demodulating circuit are arranged to the signal transmitting unit 464 on the main body portion side and the signal transmitting unit 465 on the cord side which demodulate the superimposed signal and convert the signal into the video signal.

The electric signal such as the video signal is transmitted by the signal transmitting unit 464 on the main body portion side having the transformer T3 and the signal transmitting unit 465 on the cord side having the transformer T4. Thus, the number of transformers used for the transmission is one from two in the cord connecting portion 40 and the main-body-portion connecting portion 42, and the connector portion is reduced in size.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
an endoscope, the endoscope comprising:
a main body unit in which a charge coupled device, a control unit, signal lines, a first earth electric wire and a light guide are arranged, and including a connecting portion which is formed by collecting a first electric contact, a first non-contact power transmitting portion serving as a non-contact electromagnetic induction and coupling device, a first non-contact signal transmitting portion, and a first illumination light transmitting portion, a and
a universal cord unit in which a second earth electric wire, signal lines, a power supply and a light guide are inserted, the universal cord unit including at one end portion which is detachably connected to the connecting portion of the main body unit, a second electrical contact being connected to the second earth electric wire, which is connectable to the first electric contact of the main body unit, a second non-contact power transmitting portion and a second non-contact signal transmitting portion respectively connected to the first non-contact power transmitting portion and the first non-contact signal transmitting portion of the main body unit, and a second illumination light transmitting portion connectable to the first illumination light transmitting option of the main body, unit and the universal cord unit including a scope connector at another end portion; and
an endoscope control device, the endoscope control device comprising:
a multi-connector portion to which the scope connector of the universal cord unit is detachably arranged, and
a video signal processing unit which controls the control unit of the endoscope.

2. An endoscope system according to claim 1, wherein two or more of the non-contact power transmitting portions, the non-contact signal transmitting portions, an electric wire connecting portion for an electric knife, and an illuminating light transmitting portion are combined, and are arranged to a connecting portion of the universal cord unit and a connecting portion of the main body unit.

3. An endoscope system according to claim 2, wherein the electric wire connecting portion for the electric knife comprises a high-frequency connecting unit.

4. An endoscope system according to claim 2, wherein the non-contact power transmitting portions and the non-contact signal transmitting portions comprising the electromagnetic induction and coupling device are coaxially arranged with the illuminating light transmitting portion as center.

5. An endoscope system according to claim 4, wherein the non-contact power transmitting portions and the non-contact signal transmitting portions comprising the electromagnetic induction and coupling device are coaxially arranged to the scope connector and the multi-connector portion with the illuminating light transmitting portion as center, and further comprising a peripheral groove being arranged relative to the scope connector, and a ball plunger being arranged relative to the multi-connector portion, corresponding to the peripheral groove.

6. An endoscope system according to claim 1, wherein an LED, which is lit-on by power obtained via the non-contact power transmitting portions, is arranged to the main body unit.

7. An endoscope system according to claim 1, wherein the non-contact power transmitting portions and the non-contact signal transmitting portions comprise a common electromagnetic induction and coupling device.

8. An endoscope system comprising:
an endoscope in which:
an image pick up device,
a control unit,
signal lines,
a first earth electric wire and a light guide are arranged, and including a scope connector formed by collecting a first electric contact, a first non-contact power transmitting portion serving as a non-contact electromagnetic induction and coupling device, a first non-contact signal transmitting portion, and a first illumination light transmitting portion, and an endoscope control device comprising:
a multi-connector portion to which the scope connector is detachably connected;
a second electrical contact, which is provided in the multi-connector portion and connectable to the first electric contact;
a second non-contact power transmitting portion and a second non-contact signal transmitting portion which are provided in the multi-connector portion and connectable to the first non-contact power transmitting portion and the first non-contact signal transmitting portion respectively, and
a video signal processing unit for controlling the control unit of the endoscope.

* * * * *